United States Patent
Schoenmeyer et al.

(10) Patent No.: US 9,177,378 B2
(45) Date of Patent: *Nov. 3, 2015

(54) UPDATING LANDMARKS TO IMPROVE COREGISTRATION AS REGIONS OF INTEREST ARE CORRECTED

(71) Applicant: Definiens AG, Munich (DE)

(72) Inventors: Ralf Schoenmeyer, Gilching (DE); Mehmet Yigitsoy, Munich (DE); Nicolas Brieu, Munich (DE)

(73) Assignee: Definiens AG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/745,476

(22) Filed: Jun. 22, 2015

(65) Prior Publication Data
US 2015/0287194 A1    Oct. 8, 2015

Related U.S. Application Data

(63) Continuation-in-part of application No. 13/764,539, filed on Feb. 11, 2013, now Pat. No. 9,060,672.

(51) Int. Cl.
| | |
|---|---|
| *G06K 9/00* | (2006.01) |
| *G06T 7/00* | (2006.01) |
| *G06F 3/0484* | (2013.01) |
| *G06F 3/0488* | (2013.01) |

(52) U.S. Cl.
CPC ............ *G06T 7/0012* (2013.01); *G06F 3/0488* (2013.01); *G06F 3/04842* (2013.01); *G06F 3/04845* (2013.01); *G06T 7/0032* (2013.01); *G06T 7/0081* (2013.01); *G06T 2207/10056* (2013.01); *G06T 2207/30024* (2013.01); *G06T 2207/30096* (2013.01)

(58) Field of Classification Search
None
See application file for complete search history.

(56) References Cited

U.S. PATENT DOCUMENTS

| | | | |
|---|---|---|---|
| 7,995,864 B2 | 8/2011 | Mullick et al. | 382/294 |
| 8,165,425 B2 | 4/2012 | DeClerck | 382/294 |
| 8,200,316 B2 | 6/2012 | Keppel et al. | 600/436 |
| 8,620,086 B2 | 12/2013 | Lam et al. | 382/190 |
| 8,855,748 B2 | 10/2014 | Keppel et al. | 600/436 |
| 2003/0208116 A1 | 11/2003 | Liang et al. | 600/407 |
| 2010/0172556 A1 | 7/2010 | Cohen et al. | 382/128 |
| 2010/0183213 A1* | 7/2010 | Keppel | A61B 6/037 382/131 |

(Continued)

OTHER PUBLICATIONS

Sahba et. al, A coarse-to-fine approach to prostate boundary segmentation in ultrasound images, BioMedical Engineering OnLine 2005, 4:58 doi:10.1 186/1475-925X-4-58.*

*Primary Examiner* — Tahmina Ansari
(74) *Attorney, Agent, or Firm* — Imperium Patent Works; Darien K. Wallace

(57) ABSTRACT

The coregistration of digital images of tissue slices is improved by updating landmarks based on the manual outlining of regions of interest on the images. A first image of a first slice is coarsely coregistered with a second image of a second slice using a first landmark on the first image and a second landmark on the second image. A user manually outlines a first region of interest on the first image. The outline is positioned over a second region of interest on the second image using the second landmark. The user manually moves a contour point of the outline on the second image to form a corrected outline. The second landmark is moved based on how the contour point was manually moved so that the first and second images are more finely coregistered after the second landmark is moved. Each state of corrected contour points and landmarks is saved.

20 Claims, 26 Drawing Sheets

(56) References Cited

U.S. PATENT DOCUMENTS

| | | | |
|---|---|---|---|
| 2013/0016886 A1* | 1/2013 | Schoenmeyer | G06T 7/0012 382/128 |
| 2013/0034202 A1 | 2/2013 | Keppel et al. | 378/37 |
| 2013/0170726 A1* | 7/2013 | Kaufman | G06T 3/0068 382/131 |
| 2014/0073907 A1 | 3/2014 | Kumar et al. | 600/414 |
| 2014/0228707 A1 | 8/2014 | Brieu et al. | 600/567 |
| 2014/0378500 A1 | 12/2014 | Cohen et al. | 514/291 |

* cited by examiner

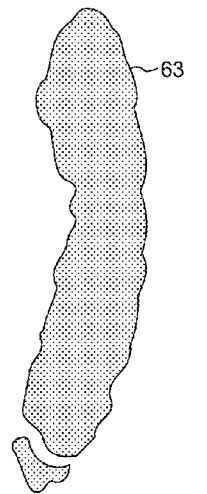 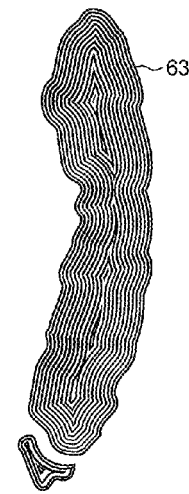 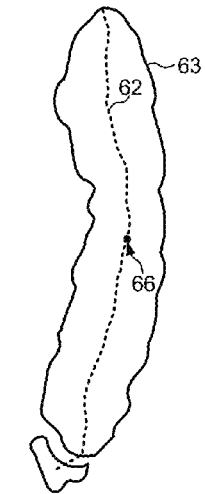 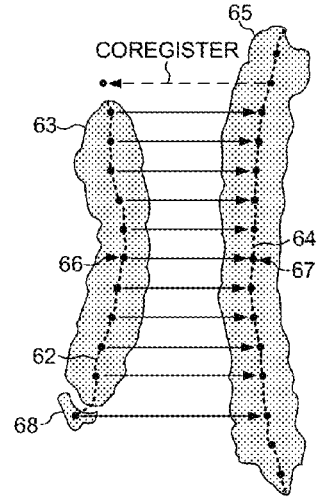
FIG. 7A   FIG. 7B   FIG. 7C   FIG. 7D
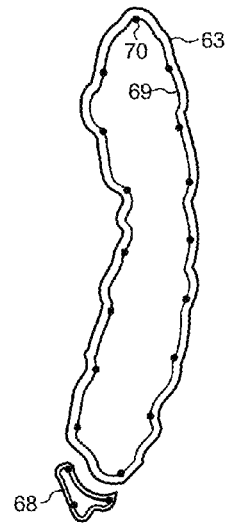
FIG. 8

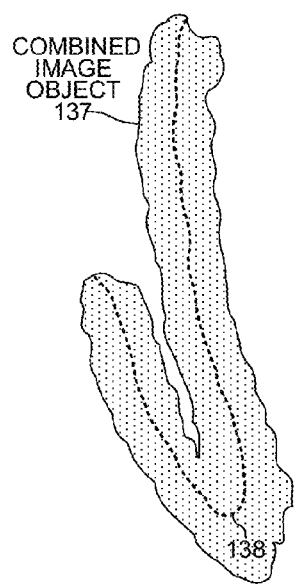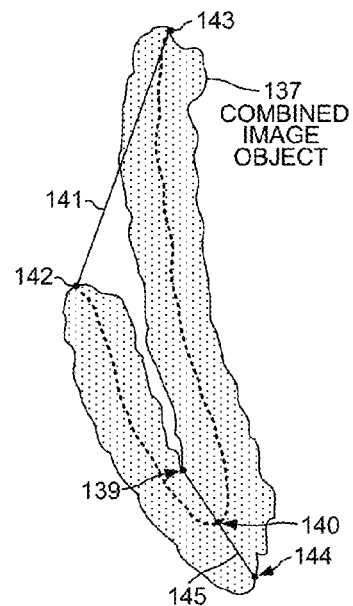
FIG. 18A  FIG. 18B
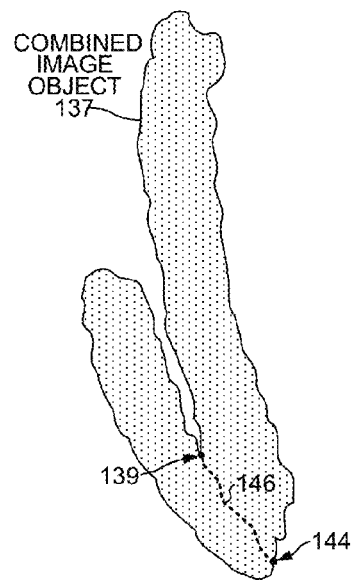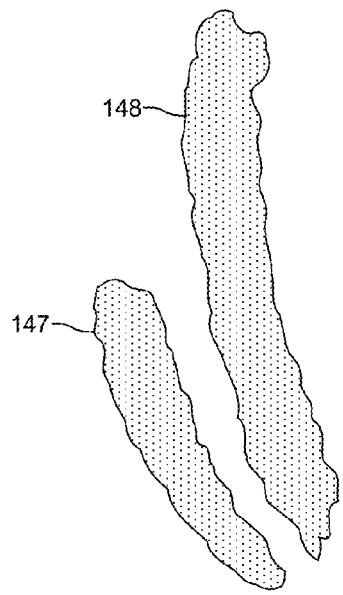
FIG. 18C  FIG. 18D

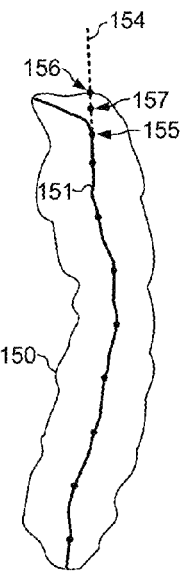
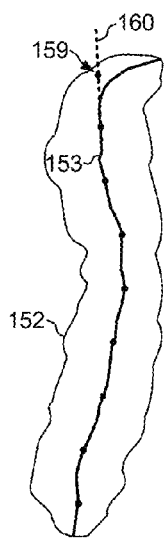
FIG. 19A          FIG. 19B
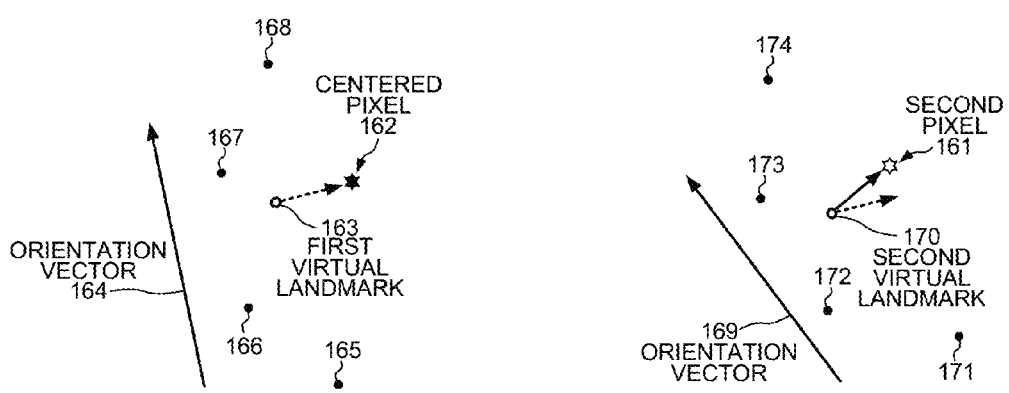
FIG. 20

$$\Delta M_i = \sum_{j=1}^{|P|} w_j r_j \tau_j \qquad (247)$$

$$w_j = \frac{\|\tau_j\|}{\|\tau_j\| + \|d_{i,j}\|^2} \qquad (248)$$

$$r_j = 1 - \frac{\|d_{i,j}\|^2}{\sum_{k=1}^{|P|} \|d_{i,k}\|^2} \qquad (249)$$

$$\tau_j = Q_j - T(P_j) \qquad (250)$$

$$d_{i,j} = M_i - T(P_j) \qquad (251)$$

UPDATING LANDMARKS TO IMPROVE COREGISTRATION AS REGIONS OF INTEREST ARE CORRECTED

CROSS REFERENCE TO RELATED APPLICATION

This application is a continuation-in-part of, and claims priority under 35 U.S.C. §120 from, nonprovisional U.S. patent application Ser. No. 13/764,539 entitled "Coregistering Images of Needle Biopsies Using Multiple Weighted Landmarks," now U.S. Pat. No. 9,060,672, filed on Feb. 11, 2013, the subject matter of which is incorporated herein by reference. updating landmarks to improve coregistration as regions of interest are drawn

TECHNICAL FIELD

The present invention relates to coregistering digital images of tissue slices stained by different biomarkers.

BACKGROUND

There are many applications for analyzing tissue samples that are stained with multiple biomarkers. How the same tissue reacts to staining by different biomarkers is determined by slicing the tissue into multiple very thin slices and then separately staining the slices. In order to determine how different biomarkers stain the same tissue structures, however, digital images of the slices must be coregistered to indicate which tissue structures in one slice correspond to similar tissue structures in the other slices. Coregistration of the digital images is possible only if the thickness of the slices is thin enough so that cross sections of the same tissue structures appear in the digital images of multiple slices. For example, multiple slices may pass through a single cancerous region of tissue, and it may be possible to determine that the various outlines of the cancerous region correspond to the same cancerous region in another image even though the outlines are not identical. Coregistration of the digital images involves mapping of pixels from the digital image of one slice to the related pixels of the digital image of an adjacent slice or nearby slice.

A particular complication arises when the digital images to be coregistered include cross sections of multiple needle core biopsy samples as opposed to a continuous slice of tissue. As the slices of the multiple paraffin-embedded needle biopsy samples are cut, the elongated needle tissue samples bend, shift, stretch and become generally distorted. Most importantly, different slices of the same needle tissue sample are distorted differently. So the task of coregistering the digital images of adjacent or nearby needle tissue samples requires much more than merely determining the x-y translation and rotation of one image with respect to the other image. Because the tissue slices are distorted, each pixel of one image must be separately coregistered to the appropriate pixel in the other image.

One method of separately coregistering each pixel of one image with the associated pixel of the other image is to segment, classify and identify sufficiently small corresponding tissue structures throughout each of the digital images. The pixels are coregistered by determining the correspondence between tissue structures in the images. However, determining corresponding low-order tissue structures, such as cells, is computationally intensive at full resolution because digital images of tissue slices typically have a very high spectral resolution, which can be on the order of several Giga-pixels. In addition, these low-order tissue structures are not consistent from slice to slice; a cell in one slice does not necessarily appear in another slice. Performing segmentation on all of the structures in the images of multiple slices and then comparing each low-order structure in each image to all of the low-order structures in the other images to find corresponding low-order structures is typically not computationally feasible.

One solution for reducing computation time and improving consistency of the structures that are used for coregistration is to perform segmentation on low-resolution superimages of the tissue slices. Higher-order structures are then used for the coregistration, such as stromal-tissue regions, fatty-tissue regions, cancerous regions or connective-tissue regions. The structures of highest order in the digital images are the tissue samples themselves, whose outlines can be used for coregistration. But coregistration performed using higher-order structures is consequently imprecise because of their possible distortion from slice to slice.

A more precise method of coregistering images of needle biopsy tissue samples is sought that does not require the segmentation of all of the tissue structures in the various tissue slices. Moreover, a method is sought for displaying the various different staining results that simultaneously depicts corresponding structures in the various digital images of differently stained tissue.

SUMMARY

A system for coregistering images of tissue slices improves upon the quality of an initial coregistration by using user interaction that is performed for purposes unrelated to coregistration. The system implements a method for improving the coregistration of images of tissue slices by updating landmarks based on the manual correction of outlines over regions of interest in the images. First and second digital images of first and second tissue slices are displayed on a graphical user interface. The first and second tissue slices are stained with first and second biomarkers. Digital image analysis coarsely coregisters the first digital image with the second digital image using a first landmark on the first digital image and a second landmark on the second digital image. A user manually draws an outline over a first region of interest on the first digital image. A statistical value such as a staining score is generated for each region of interest.

Then the outline is positioned over a second region of interest on the second digital image using the second landmark. The user manually moves a first contour point of the outline on the second digital image to form a corrected outline. The corrected outline is displayed over the second region of interest on the graphical user interface. The second landmark is moved based on how the first contour point was manually moved so that the first digital image is more finely coregistered with the second digital image after the second landmark is moved.

The state of each correction version of the landmarks and contour points is saved so that subsequent corrections can be undone and returned to a prior state. The second landmark has an original location in a first coregistration state when the second digital image is coarsely coregistered with the first digital image. The second landmark has a new location after the second landmark is moved. The new location of the second landmark and a first moved location of the moved contour point are saved as part of a second coregistration state. Then the contour point of the outline is manually moved an additional time. The system can undo the last corrections and return to the second coregistration state by displaying the moved contour point at the first moved location.

In another embodiment, a method for coregistering images involves defining middle paths through image objects depicting tissue slices of needle biopsies. First landmarks are defined on a first middle path through a first image object in a first digital image of a first tissue slice, and second landmarks are defined on a second middle path through a second image object of a second digital image of a second tissue slice. Individual first landmarks are associated with individual second landmarks. A first pixel in the first object is coregistered with a second pixel in the second object using multiple first and second landmarks. The first image is displayed in a first frame on a graphical user interface, and the second image is displayed in a second frame such that the first pixel is centered in the first frame, the second pixel is centered in the second frame, and the images have the same orientations.

In one specific example, a method for coregistering digital images involves defining a first path in a first image object of a first digital image of a first tissue slice. A second path is then defined in a second image object of a second digital image of a second tissue slice. First landmarks are defined on the first path, and second landmarks are defined on the second path. An additional first landmark that is not on the first path but is within the first image object is defined at a location determined based on a local direction of the first path. Individual first landmarks are associated with individual second landmarks. A first pixel in the first image object is coregistered with a second pixel in the second object using multiple first landmarks and multiple second landmarks. The first digital image is displayed in a first frame and the second digital image is displayed in a second frame on a graphical user interface. The first pixel is positioned at a first reference location inside the first frame, and the second pixel is positioned at a second reference location inside the second frame such that the first reference location relative to the first frame corresponds to the second reference location relative to the second frame. In one aspect, the first path passes through the first image object halfway between opposite boundaries of the first image object. In another aspect, the first path resembles an outer contour of the first image object.

The coregistration of the digital images is manually adjusted after the images are displayed on the graphical user interface. The user first selects one of the second digital images displayed in a row of frames. The selected second digital image is then shifted based on user input while the first digital image does not move relative to the first frame. The first pixel at the first reference location is then coregistered with a third pixel that is positioned at the second reference location inside the second frame as a result of the shifting.

In addition to manually adjusting the coregistration by shifting the second digital image so as to coregister the third pixel with the first pixel, the second digital image is also rotated about the third pixel such that the second digital image is coregistered with the first digital image. The image objects in the second digital image that are visible in the second frame become aligned with the corresponding image objects in the first digital image. Thus, the user of the coregistration system manually shifts and rotates individual second images so as to improve the coregistration of the displayed portions of the images.

In another embodiment, a method for coregistering images defines middle paths through image objects that depict tissue slices of needle biopsies. First landmarks are defined on a first middle path through a first image object of a first digital image of a first tissue slice, and second landmarks are defined on a second middle path through a second image object of a second digital image of a second tissue slice. Individual first landmarks are associated with individual second landmarks. A first pixel in the first image object is coregistered with a second pixel in the second object using multiple first landmarks and multiple second landmarks. The first digital image is displayed in a first frame on a graphical user interface, and the second digital image is displayed in a second frame on the graphical user interface such that the first pixel is centered in the first frame and the second pixel is centered in the second frame.

The second digital image is shifted within the second frame in response to a user shifting the first digital image relative to the first frame such that each pixel of the second digital image that is centered in the second frame corresponds to a coregistered pixel of the first digital image that is centered in the first frame. The second digital image is shifted within the second frame in response to either the user shifting the first digital image under the first frame or the user shifting the first frame over the first digital image.

The coregistering of the first and second pixels is performed such that a spatial relationship between the second pixel and multiple second landmarks corresponds to the spatial relationship between the first pixel and multiple first landmarks. The spatial relationship between the first pixel and the multiple first landmarks is defined by assigning a larger weighting to those first landmarks that are closer to the first pixel. Not only is the first pixel that is centered in the first frame coregistered with the second pixel that is centered in the second frame, but the second digital image is also displayed in the second frame in a coregistered orientation to how the first digital image is displayed in the first frame. The image object that is centered in the second frame is aligned with the image object that is centered in the first frame.

In one implementation, each coregistered pixel of the second digital image is determined using landmarks that are weighted based on their distance from the each of the coregistered pixels. In another implementation, each coregistered pixel of the second digital image is determined based only on those second landmarks that are associated with first landmarks located on a particular image object.

In another embodiment, pixels in different digital images of tissue slices are coregistered using multiple landmarks that are located along middle paths of image objects. A first tissue slice and a second tissue slice are taken from a needle biopsy. A first digital image of the first tissue slice is displayed on a graphical user interface such that an area of the first digital image is enclosed by a frame. A portion of a second digital image of the second tissue slice is also displayed on the graphical user interface. The displayed portion of the second digital image has the shape of the frame and corresponds to the area of the first digital image that is enclosed by the frame. A pixel that is centered in the displayed portion of the second digital image is initially coregistered with an associated pixel of the first digital image that is centered in the frame by using multiple second landmarks in the second digital image and multiple associated first landmarks in the first digital image. The displayed portion of the second digital image is shifted in response to a user shifting the first digital image relative to the frame such that each coregistered pixel of the displayed portion of the second digital image is determined using first landmarks that are weighted based on their distances to the associated pixel of the first digital image that is centered in the frame.

As the user shifts the first digital image under the frame or the frame over the first digital image, each pixel that is centered in the displayed portion of the second digital image corresponds to a coregistered pixel of the first digital image that is centered in the frame. The pixels of the displayed portion of the second digital image are dynamically coregistered as the user shifts the first digital image such that the pixel that is centered in the displayed portion is coregistered with the pixel that is centered in the frame using only on those second landmarks that are associated with first landmarks located on an image object.

In another embodiment, the pixels of the displayed portion of the second digital image are dynamically coregistered with pixels of the first digital image as the user zooms in the first digital image within the frame such that the pixel that is centered in the displayed portion is coregistered with the pixel that is centered in the frame by using only those second landmarks that are associated with first landmarks located inside the frame. When coregistration is performed using only those second landmarks associated with first landmarks located inside the frame, the displayed portion of the second digital image is displayed in a coregistered orientation to how the first digital image is oriented in the frame.

Other embodiments and advantages are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

FIG. 6A shows an image object with low linearity.

FIG. 6B shows the object of FIG. 6A with a splitting line that connects concave points along its boundary.

FIG. 6C shows two split portions of the object after they have been separated using the concave points.

FIG. 6D shows an image object with a high angle of curvature.

FIG. 6E shows the object of FIG. 6D with a splitting line between a strong concave point and a weak concave point.

FIG. 6F shows two split portions of the object after they have been separated along the splitting line.

FIGS. 7A-D illustrate a process by which the system of FIG. 1 defines a middle path through an image object. FIG. 7A shows an image object that represents one of several slice sections of a tissue slice.

FIG. 7B shows the step of incrementally shrinking the object by the same small steps from all sides in order to obtain the middle path.

FIG. 7C shows a center landmark on the middle path through the object.

FIG. 7D shows first landmarks on a middle path through one object and second landmarks on a middle path through another object.

FIG. 8 shows a loop path in an image object on which landmarks are placed.

FIG. 17A shows an image object with low linearity that will be separated using concave points.

FIG. 17B illustrates a method of finding a middle path by incrementally shrinking the image object of FIG. 17A.

FIG. 17C shows the longest middle path on the image object of FIG. 17A.

FIG. 17D illustrates a method for finding the middle path width of the image object of FIG. 17A.

FIG. 17E shows splitting paths that connect points at the centers of concave curves on the image object of FIG. 17A.

FIG. 17F shows the image object of FIG. 17A after it has been split into two portions that have the greatest combined linearity.

FIGS. 18A-D illustrate a way to separate a combined image object that is curved as opposed to branched. FIG. 18A shows a curved combined object and its middle path.

FIG. 18B shows a concave point on the boundary and a nearby point at the highest local curvature on the middle path of the object of FIG. 18A.

FIG. 18C shows a splitting path that connects a concave point and an intersecting point and that is used to split the object of FIG. 18A.

FIG. 18D shows the object of FIG. 18A after being split along the splitting path shown in FIG. 18C.

FIGS. 19A-B illustrate how landmarks are placed along corrected middle paths of image objects. FIG. 19A shows an image object with a middle path that has been corrected by extending the path in a local direction.

FIG. 19B shows a paired image object to the image object of FIG. 19A.

FIG. 20 illustrates a procedure for coregistering a second pixel with a first pixel using virtual landmarks generated by weighting a plurality of first and second landmarks.

DETAILED DESCRIPTION

Reference will now be made in detail to some embodiments of the invention, examples of which are illustrated in the accompanying drawings.

Figure 1:
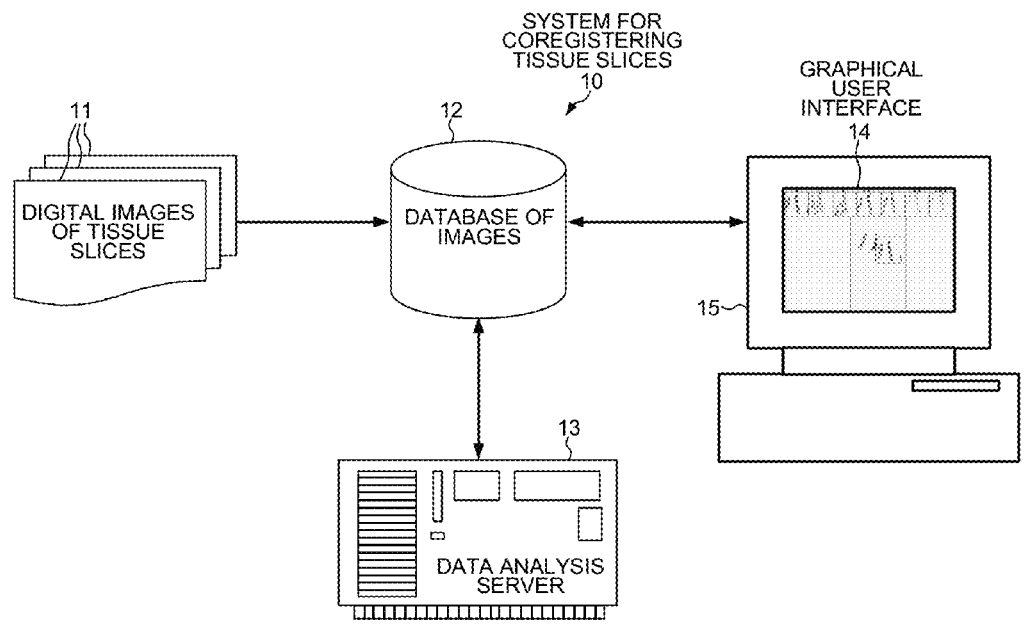
FIG. 1 is a diagram of a novel system for coregistering digital images of tissue slices obtained from needle biopsies.

FIG. 1 shows a system 10 for coregistering digital images of tissue slices obtained from needle biopsies. Tissue slices of needle biopsies are obtained as described below. Then digital images 11 of the tissue slices are acquired at high magnification. The acquired digital images 11 are stored in a database 12 of images. Image analysis software executing on a data analysis server 13 then performs intelligent image processing and automated classification and quantification. The image analysis software is a computer program product tangibly embodied on a computer-readable storage medium in server 13 and comprises computer readable and executable program instructions that when executed by a processor on server 13 provide a visual display on a graphical user interface 14 of an interconnected display device 15, such as a personal computer. The image analysis software transforms unlinked input data in the form of pixels into a hierarchical network of objects.

System 10 analyzes, coregisters and displays the digital images 11 of tissue slices in a coregistered orientation such that centered, coregistered image objects in multiple images are aligned. The image analysis program prepares links between some objects and thereby generates higher hierarchically ranked objects. The image analysis program provides the higher hierarchically ranked objects with properties, classifies them, and then links those objects again at a still higher level to other objects. The higher hierarchically ranked objects are used to find target objects in the images more rapidly. More easily detected starting objects are found first and then used to identify hard-to-find objects in the hierarchical data structure.

Both general and subject-specific knowledge is used to classify and segment objects in the images. The knowledge and the program flow of the image analysis program are separated in the software structure. The parameters by which the image analysis is performed, for example thresholds of brightness or size, can be changed without having to revise the process hierarchy of software steps. The image analysis software displays both the original digital images 11 as well as the corresponding processed segmented images on the graphical user interface 14. Classified and segmented objects in the digital images are marked or highlighted to correspond to their classification. For example, objects that have a membership in the same class are depicted in the same color. Besides performing object-oriented processing, the image analysis software also performs pixel-oriented processing. The results of the pixel-oriented processing are visualized by differently colored pixels representing values from local statistical results, such as heat maps.

Figure 2:
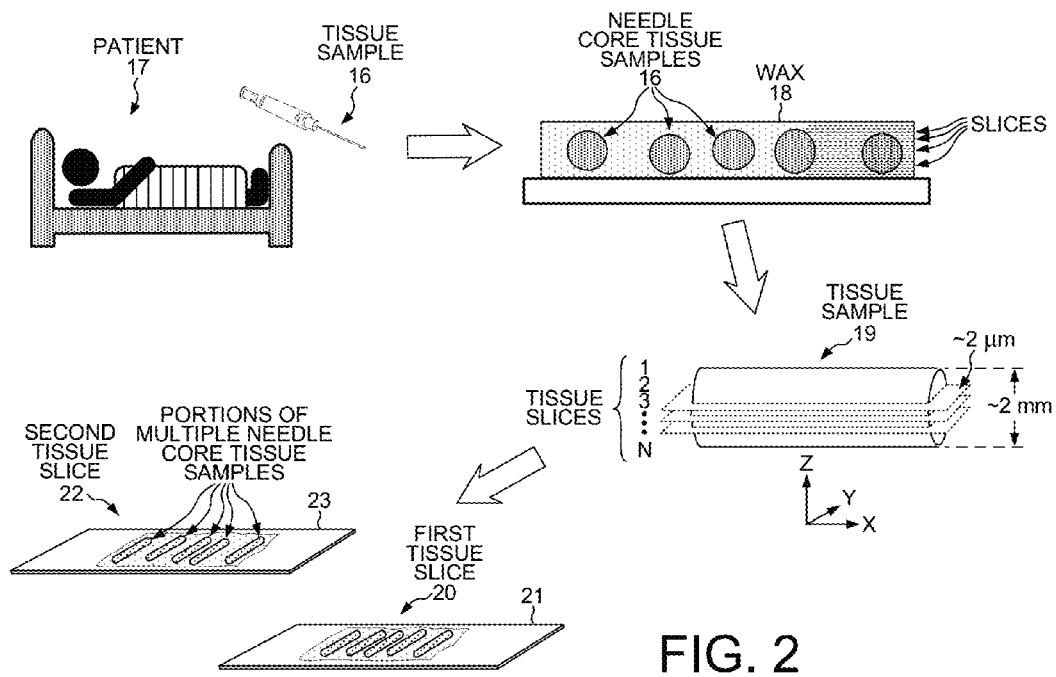
FIG. 2 illustrates the process for acquiring the digital images that are then coregistered and displayed by the system of FIG. 1.

FIG. 2 illustrates the process for acquiring the digital images 11 that are then segmented, classified, coregistered and displayed by system 10. Tissue samples 16 are typically taken from a live patient 17 in the form of a biopsy. Biopsies are taken either as resection biopsies during surgery on the patient or as needle biopsies in an outpatient procedure. System 10 is specially adapted to coregister digital images of tissue samples obtained from needle biopsies. For example, needle biopsies are typically used to obtain samples of prostate and breast tissue that is to be tested for cancer. For diagnosing prostate cancer, most doctors agree that an initial prostate biopsy should include at least ten to twelve needle core samples. The needle core tissue samples 16 are embedded in paraffin wax 18, and then the entire block of paraffin-embedded samples is sliced into many adjacent thin planar slices.

FIG. 2 shows a single cylindrical tissue sample 19 that is sliced into N adjacent planar tissue slices. Needle core tissue sample 19 is roughly two millimeters in diameter, and each of the tissue slices has a thickness of about two microns. Thus, it is possible to obtain about a thousand tissue slices from each tissue sample 19. Because the slices are very thin, adjacent slices contain parts of the same tissue structures. The slices include tissue structures at different z altitudes at the same position in the x and y dimensions of the tissue sample. But the entire block of paraffin-embedded samples, as opposed to each individual cylindrical sample, is sliced into many tissue slices. Thus, each tissue slice includes a cross section of several needle core tissue samples 16.

FIG. 2 shows a first tissue slice 20 placed on a first slide 21 as well as a second tissue slice 22 placed on a second slide 23. Second tissue slice 22 originated from the block of paraffin-embedded samples adjacent to first tissue slice 20. Before being put on a slide, each of the tissue slices can be stained with one or more different biomarkers. The same tissue reacts uniquely to each different biomarker. For example, various slices can be stained with hematoxylin and eosin (H&E), cytokeratin 18 (CK18), transcription factor p63, Human Epidermal growth factor Receptor 2 (Her2), Her2/neu cytoplasmic stain, estrogen receptor (ER) stain, progesterone receptor (PR) stain, tumor marker Ki67, Mib, SishChr17, SishHer2, cluster of differentiation 44 (CD44) antibody stain and CD23 antibody stain. A high resolution digital image 11 is then taken of each stained slice.

Figure 3:
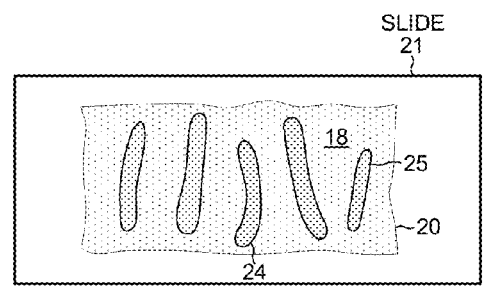
FIG. 3 shows a slide containing a tissue slice of five needle biopsies.

FIG. 3 shows first tissue slice 20 on first slide 21 in more detail. Although the several needle core tissue samples 16 are aligned nearly in parallel in the wax block, the tissue samples are shifted, stretched and distorted as each slice is cut because the wax 18 is softer than the tissue. For example, the slice section 24 of one of the needle core tissue samples 16 appears banana-shaped on slide 21. Moreover, not all of the needle core tissue samples 16 are suspended at the exact same elevation in the block of wax 18 as shown in FIG. 2, so the area of the cross section of a sample will be smaller if the slice section passes through the needle core tissue sample 16 nearer to the top or nearer the bottom. In FIG. 3, a slice section 25 has a smaller area than that of slice section 24 because the tissue sample from which slice section 25 was taken was suspended higher or lower in the wax. The distortion in the slice sections 24-25 caused when a blade cuts through first tissue slice 20 makes it more difficult to coregister the slice sections 24-25 with the corresponding sections in other slices above and below first tissue slice 20. System 10 is specially adapted to coregister digital images containing these distorted tissue slices from needle biopsies.

Figure 4:
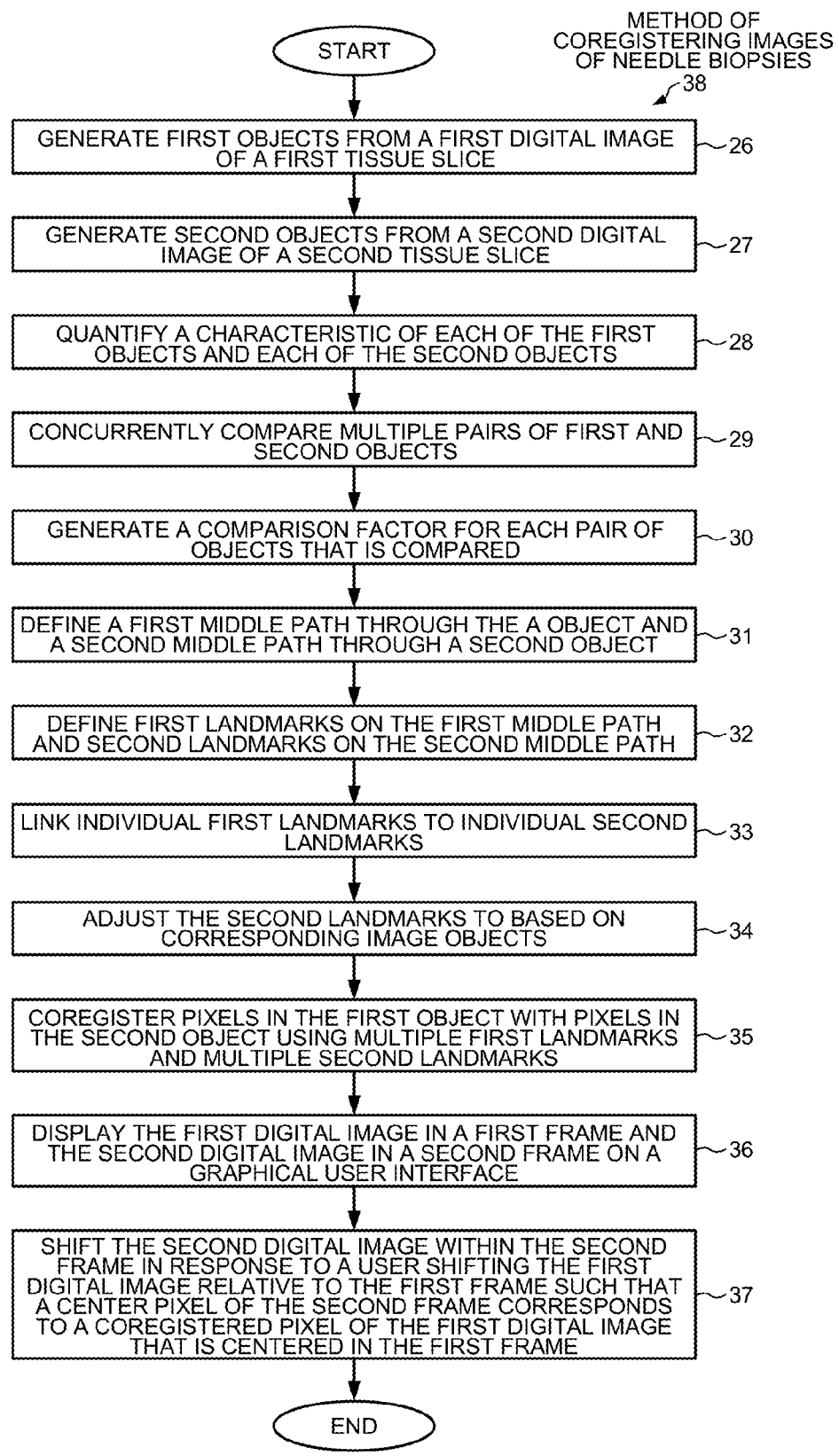
FIG. 4 is a flowchart of steps for coregistering digital images of tissue slices obtained from needle biopsies.

FIG. 4 is a flowchart of steps 26-37 of a method 38 for coregistering digital images of tissue slices obtained from needle biopsies. The digital images are acquired by using a digital camera, a high-resolution light microscope or a slide scanner. A typical digital image of a tissue slice has a resolution of many billions of pixels.

In a first step 26, first image objects are generated from a first digital image 39 taken of first tissue slice 20. The image objects are not merely objects apparent in an image. Rather, the image objects are objects in a data network comprising linked pixels.

Figure 5:
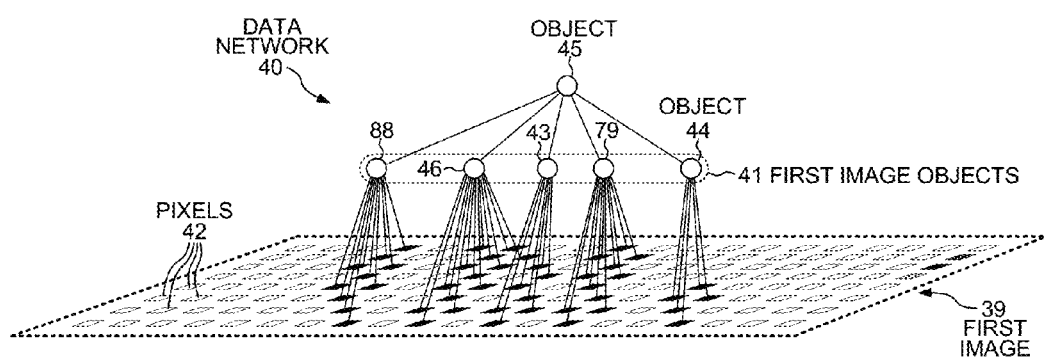
FIG. 5 illustrates a data network generated by the system of FIG. 1 in which image objects of the data network are linked to selected pixels of an image of a tissue slice.

FIG. 5 illustrates exemplary data network 40 that is generated by system 10. In step 26, system 10 generates first image objects 41 from first digital image 39 based on the slices of the needle biopsies. The image analysis program of system 10 uses object-oriented image analysis to generate objects of data network 40 by linking selected pixels 42 to objects according to a process hierarchy of steps and algorithms and according to a classification network. For a more detailed description of generating a data network using a process hierarchy and a class network, see U.S. Pat. No. 8,319,793, the contents of which are incorporated herein by reference. Each digital image comprises pixel values associated with the locations of each of the pixels 42. Thus, a pixel represents a position or spatial location on a digital image. The image analysis program operates on the digital pixel values and links the pixels to form objects. Each object is linked to a set of pixel locations based on the associated pixel values. For example, an object is generated by linking to the object those pixels having similar characteristics, such as hue, saturation and brightness as defined by the pixel value. Thresholds of brightness at pixel locations that are grouped together can be obtained from a histogram of the pixel values in the digital image. The pixels form the lowest hierarchical level of data network 40. In FIG. 5, an image object 43 corresponds to slice section 24, and an image object 44 corresponds to slice section 25. Objects 43-44 are in turn linked to object 45 in a higher hierarchical level of data network 40.

FIG. 5 also illustrates another difficulty in coregistering images of needle biopsies in addition to the distortion caused by slicing paraffin-embedded tissue samples. Some slices of tissue samples may be shifted in the x and y dimensions during the slicing such that the tissue slices are contacting each other in the digital images. In addition, multiple tissue samples may overlap each other because on tissue sample crossed over another tissue sample in the block of wax. Image object 43 is in contact with an image object 46. Before individual portions of needle core tissue samples can be coregistered, the boundary of each tissue sample must be determined by separating multiple tissue samples that are in contact. Image object 43 must be separated from image object 46 before each of these image objects can be coregistered with corresponding image objects in other slices of the paraffin-embedded tissue samples.

Figure 6A:
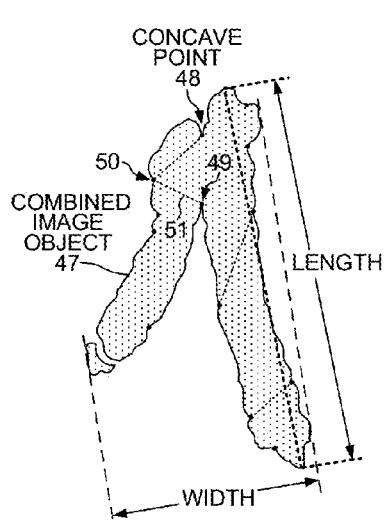
FIGS. 6A-F illustrate ways of separating image objects of tissue samples that are in contact with or overlap each other.
Figure 6B:
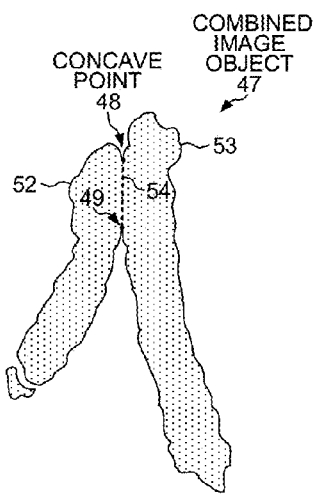
Figure 6C:
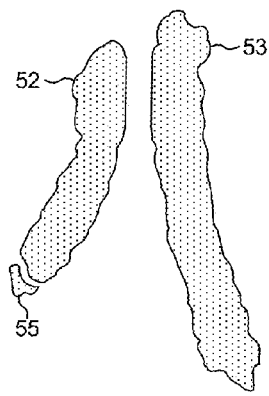

FIGS. 6A-F illustrate two possible ways of separating image objects of tissue samples that are in contact with or overlap each other. Additional ways of separating image objects are described below with regard to FIGS. 17-18. FIGS. 6A-C show how a combined image object 47 is separated into its constituent tissue samples using concave points in the combined object. First, objects with a low linearity are identified. An object has a low linearity when it has a large ratio of its narrowest total width to its longest dimension. Combined image object 47 is identified as an object with a low linearity. The length and width of combined image object 47 are indicated in FIG. 6A. Next, points are identified at the center of concave curves along the boundary. Some of the concave points, such as concave points 48-50, are indicated in FIG. 6A as dots on the boundary of combined image object 47. Then, the combined image object is split into smaller objects along splitting lines that connect the concave points along the boundary. For example, splitting line 51 connects concave points 49 and 50. Finally, only those split portions of a combined object are retained that have the greatest combined linearity. For example, splitting line 51 does not result in two split portions having the greatest combined linearity.

FIG. 6B shows combined image object 47 that has been split into the two split portions 52-53 that have the greatest combined linearity. Split portions 52-53 are formed by separating object 47 along a splitting line 54 that connects concave points 48 and 49. FIG. 6C shows split portion 52 and split portion 53 after they have been separated using concave points 48-49. Split portions 52-53 are logically split in data network 40 and treated as separate image objects for purposes of coregistration, but first image 39 is not altered by separating split portions 52-53 in the image. In addition to splitting combined objects that exhibit low linearity, small objects are added to larger objects if doing so increases the linearity of the resulting combined object. FIG. 6C also shows a small object 55 that is logically added to image object 52 in data network 40.

Figure 6D:
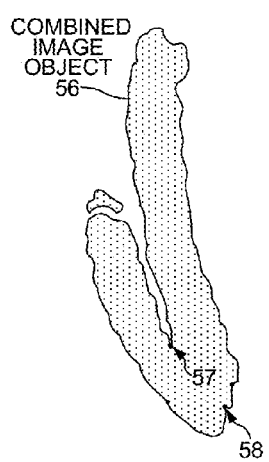
Figure 6E:
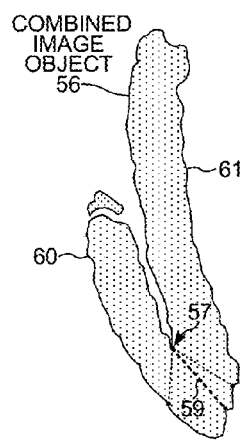
Figure 6F:
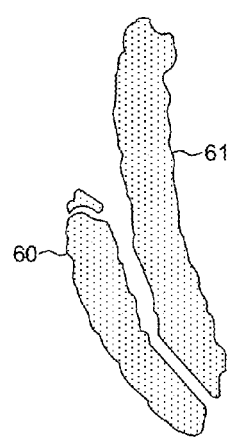

FIGS. 6D-F show how a combined image object 56 is separated into its constituent tissue samples using one strong concave points and a weak concave point. Whereas combined image object 47 was identified as requiring splitting because of its large width compared to its length, combined image object 56 is identified as requiring splitting because of its high angle of curvature. Because system 10 performs object-oriented image analysis, as opposed to pixel-oriented image analysis, the image objects can be classified according to features not evident from the pixels alone. For example, the curvature of an image object can be determined by first generating a middle path through the object and then analyzing the curvature of the middle path.

In FIG. 6D, concave points, including a strong concave point 57 and a weak concave point 58, have been identified. Combined image object 56 is split into smaller objects along splitting lines that connect strong concave point 57 to various weak concave points. For example, splitting line 59 connects concave points 57 and 58. Those split portions of combined object 56 that have the greatest combined linearity are given a higher weighting. However, a higher weighting is also assigned to those splitting lines that follow an intensity change in the pixels. In one implementation, splitting lines need not be linear but can follow a boundary of intensity change in the pixels. FIG. 6E shows combined image object 56 that has been split by splitting line 59 into the two split portions 60-61 that have the greatest combined linearity. The pixels along splitting line 59 also exhibit a different intensity. FIG. 6F shows split portion 60 and split portion 61 after they have been separated along splitting line 59. Split portions 60-61 are logically split in data network 40 and treated as separate image objects for purposes of coregistration, but first image 39 is not altered by separating split portions 60-61 in the image.

In step 27 of method 38, second image objects are generated from a second digital image taken of second tissue slice 22. The second image objects are also objects comprising linked pixels in data network 40. Second tissue slice 22 is taken from the paraffin-embedded tissue samples immediately above first tissue slice 20. Image objects are also generated from digital images of the tissue slice immediately below first tissue slice 20, as well as all of the other tissue slices sliced from the paraffin-embedded tissue samples 16. For example, if ten needle core samples are taken of a patient with prostate cancer, and the paraffin-embedded tissue samples are sliced into one thousand slices, then there are ten thousand first and second image objects from which ten chains of pairs of coregistered objects must be generated. For each of the ten needle core tissue samples, adjacent pairs of image objects are coregistered to form a chain of slice 1 to slice 2, slice 2 to slice 3, slice 3 to slice 4, etc. In the optimal implementation of method 38, only the image objects corresponding to the top and bottom slices are not coregistered with another image object. This optimal implementation generates a closed loop in which for each needle core tissue sample each image object is coregistered with at least one other image object.

In step 28, a characteristic of each of the first objects 41 and each of the second objects is quantified. Characteristics such as length, width and area of the image objects are quantified and stored in database 12. The linearity of each object can be determined from its longest dimension (length) and its narrowest total width along its entire length. All of the image objects are categorized according to similar length, width, area and linearity.

In step 29, system 10 concurrently compares multiple pairs of image objects within each group of objects having similar characteristics. Multiple pairs of image objects in different digital images are compared simultaneously. For example, those 20% of the image objects falling within a range of the largest combined length, width, area and linearity are each compared to one another. For each pair of image objects that is compared, both objects have magnitudes of a characteristic or a combined characteristic that are more similar to one another than are the two magnitudes of the characteristic or combined characteristic of all pairs of objects that are not compared. At least one of the pairs of image objects that is compared includes one of the first objects 41 and one of the second objects, such that objects in adjacent slices (and different digital images) are compared. Consequently, one of the first objects 41 and one of the second objects are in different digital images. Then the next 20% of the image objects whose combined length, width, area and linearity fall within a second range are each compared to one another. The third, fourth and fifth groups of 20% of the image objects are also compared to one another.

In step 30, a comparison factor is generated for each pair of image objects that is compared in step 29. In one implementation, the comparison factor is an overlap ratio. One way of calculating an overlap ratio is to divide the number of pixels that overlap by the total number of pixels of the combined superimposed image objects. System 10 identifies the pair of objects that has the largest comparison factor, e.g., overlap ratio. Two image objects that perfectly overlap have an overlap ratio of one. The pair of image objects with the largest overlap ratio will be the easiest to coregister, so the coregistration begins with this pair in order to conserve computational resources. This most similar pair has a first object 63 and a second object that are in different digital images.

In step 31, a first middle path is defined through first image object 63, and a second middle path is defined through the second image object. First image object 63 is in first digital image 39 of first tissue slice 20. The second image object is in a second digital image of second tissue slice 22.

FIGS. 7A-D illustrate the process by which system 10 defines a first middle path 62 through the first image object 63 in first digital image 39. FIG. 7A shows first image object 63, which represents one of several slice sections of first tissue slice 20. Middle path 62 traverses through first image object 63 along a path that is equidistant from opposite sides of the object. The route of middle path 62 is determined by incrementally shrinking object 63 by the same small steps from all sides, as shown in FIG. 7B. Where the two shrinking sides meet is the route of the middle path. Middle path 62 is shown in FIGS. 7C-D. FIG. 7D shows a middle path 64 defined through a second image object 65 in a second digital image. The route of middle path 64 is determined in the same manner as the route of middle path 62. In one implementation, the middle path need not extend all the way from one boundary of an image object to the opposite boundary. Only the middle path at the center of the object can be used. In another implementation, the middle path can be composed of multiple path segments along the route through the middle of the object.

In step 32, first landmarks are defined on first middle path 62, and second landmarks are defined on second middle path 64. First, the middle of middle path 62 is determined, and a center landmark 66 is placed at the middle of middle path 62, as shown in FIG. 7C. Then, additional first landmarks are placed on middle path 62 at constant intervals on either side of center landmark 66. FIG. 7D shows that eleven first landmarks have been defined on first middle path 62. The lowest landmark is not placed at the constant interval from its neighboring landmark, but rather is placed in the center of an object fragment 68 at the bottom of first image object 63. This ensures that a landmark will be placed in object fragment 68.

In another implementation, additional landmarks are placed at locations that are not on the middle path but rather are positioned at based on a local direction of the middle path. These additional landmarks can be located both inside or outside of the boundary of an image object. For example, the average linear direction of the bottom third of middle path 62 can be extended beyond the lower boundary of first image object 63, and an additional landmark can be placed at an appropriate interval from the last landmark along the extension line instead of at the center of object fragment 68. Thus, an additional first landmark would be placed not on middle path 62 but rather at a location determined based on a local direction of middle path 62. Moreover, landmarks at the upper and lower ends of first image object 63 can be placed not on middle path 62 but rather within object 63 at locations determined based on the local direction of middle path 62 more than one interval away from the boundary of object 63. Extending the line on which landmarks are placed near an object boundary based on the local direction of the middle path away from the boundary eliminates any ambiguities in the method of FIG. 7B for defining the path that is equidistant from "opposite" sides as that path approaches the boundary.

A center landmark 67 is also placed at the middle of middle path 64 of second image object 65, as shown in FIG. 7D. Additional second landmarks are then placed on middle path 64 at the same intervals along second middle path 64 as the first landmarks are placed along first middle path 62. As second image object 65 is longer than first image object 63, more second landmarks are placed at the top and bottom along middle path 64 at the same constant intervals. The larger interval between the tenth and eleventh first landmarks is maintained, however, between the twelfth and thirteenth second landmarks.

In step 33, individual first landmarks are linked to the corresponding individual second landmarks. As shown by the arrows in FIG. 7D, each of the eleven first landmarks is associated with one of the second landmarks.

In another embodiment, landmarks are placed along a loop path equidistant inside the boundary of the image object. For example, in another embodiment of step 31, system 10 defines a loop path 69 that travels equidistant inside the boundary of first image object 63. In step 32, landmarks are then defined at equal intervals along loop path 69. FIG. 8 shows loop path 69 defined just inside the contour of the boundary of first image object 63. Instead of defining a center landmark at the middle of an open path, a top landmark 70 is defined at the upper most point of the closed loop path 69. The landmarks are then placed at equal intervals around the loop starting at the position of top landmark 70. In step 33, individual first landmarks on a first loop path are then linked to corresponding second landmarks on a second loop path.

In step 34, the second landmarks in second image object 65 are adjusted based on corresponding image objects within second image object 65. The adjusting in step 34 uses object-oriented image analysis as opposed to merely pixel-oriented image analysis. Pixel-oriented image analysis does not segment digital images into objects whose characteristics are then determined and stored in a data network. First image object 63 is segmented and classified to generate many subobjects that correspond to tissue structures, such as a nucleus, a membrane, a cell or a group of cells. Thus, there are several hierarchical levels in data network 40 between the first image objects 41 shown in FIG. 5 and the pixels 42. Data network 40 also includes a hierarchical branch representing the second image objects from the second digital image, which in turn includes multiple hierarchical levels between the second image objects and the pixels of the second digital image.

System 10 determines the characteristics of the subobject located at the position of each first landmark and then adjusts the position of the associated second landmark to coincide with a subobject in second image object 65 that exhibits similar characteristics. However, method 38 does not require subobjects to be matched at each coregistered pixel of second image object 65 but rather only at the locations of the second landmarks. For example, if center landmark 66 is located over a nucleus exhibiting a particular length, width, area, linearity (or non-linearity) and average pixel intensity, then center landmark 67 is shifted in second image object 65 to the location of a subobject nearest to the original position of center landmark 67 that has a similar length, width, area, linearity and intensity. By linking a second landmark to the associated first landmark in step 33, the area is reduced in the second digital image in which a subobject must be found that is similar to the subobject at the location of the first landmark.

In step 35, a first pixel in first image object 63 is coregistered with a second pixel in second image object 65 using multiple first landmarks and multiple second landmarks. System 10 attempts to coregister each pixel in first image object 63 with a pixel in second image object 65. Where first image object 63 does not overlap second image object 65 when the two objects are superimposed, pixels from one object are coregistered with pixels outside of the other object. For example, the pixels located at the first and second landmarks on second image object 65 are coregistered with pixels that are outside of first image object 63, as shown in FIG. 7D.

Figure 9:
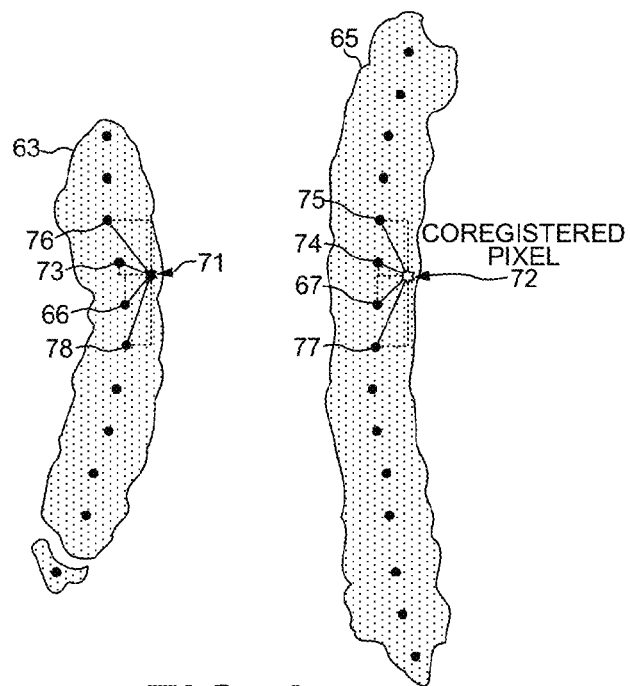
FIG. 9 illustrates a process by which a pixel in a first image object is coregistered with a pixel in a second image object using multiple landmarks on both objects.
Figure 10:
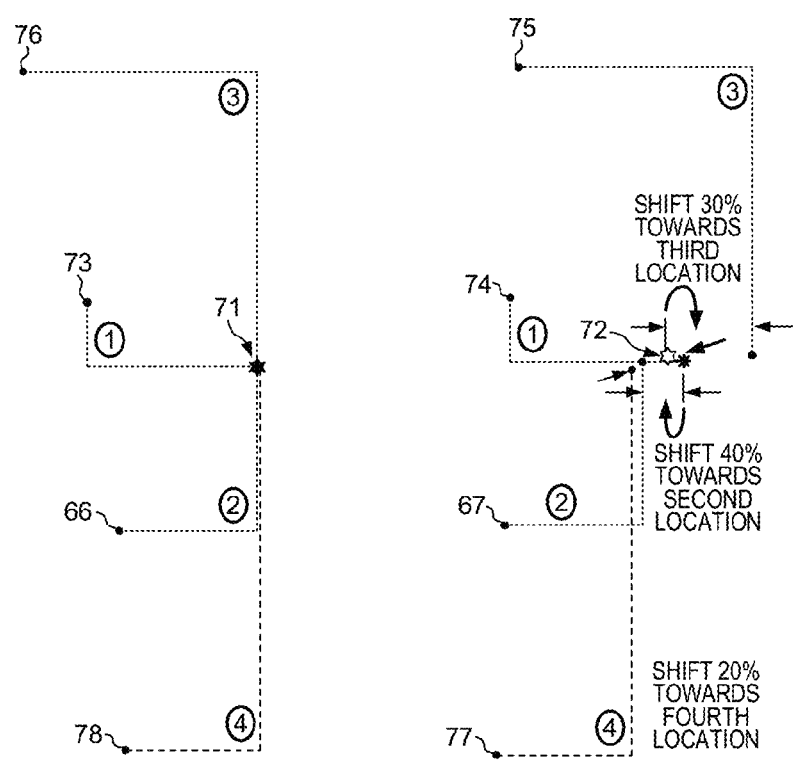
FIG. 10 is a more detailed view of eight of the landmarks used in FIG. 9 to coregister the pair of pixels.

FIG. 9 shows a first pixel 71 in first image object 63 that is coregistered with a second pixel 72 in second image object 65 using multiple first landmarks and multiple second landmarks. Second pixel 72 is identified by determining which pixel in second image object 65 has the same spatial relationships to the second landmarks as first pixel 71 has to the associated first landmarks in first image object 63. The spatial relationships to nearer landmarks are given greater weighting. First pixel 71 is closest to landmark 73. So a preliminary location (*) in second object 65 is determined that is the same distance and angle from associated landmark 74 as first pixel 71 is from landmark 73. The preliminary location (*) is shown in FIG. 10. Then the preliminary location is adjusted by a first predetermined proportion towards a second location that is the same distance and angle from associated center landmark 67 as first pixel 71 is from center landmark 66, considering that landmark 66 is the second closest landmark to first pixel 71. In one implementation, the first predetermined proportion is 40%. Thus, the preliminary location is shifted 40% of the way from the preliminary location (*) to the second location that is the same distance and angle from landmark 67 as first pixel 71 is from landmark 66.

Then the adjusted location is further adjusted by a second predetermined proportion towards a third location that is the same distance and angle from landmark 75 as first pixel 71 is from landmark 76, considering that landmark 76 is the third closest landmark to first pixel 71. In one implementation, the second predetermined proportion is 30%. Thus, the adjusted location is shifted 30% of the way to the third location that is the same distance and angle from landmark 75 as first pixel 71 is from landmark 76. And the adjusted location is further adjusted by a third predetermined proportion, such as 20%, towards a fourth location that is the same distance and angle from landmark 77 as first pixel 71 is from landmark 78 because landmark 78 is the fourth closest landmark to first pixel 71. In FIG. 10, second pixel 72 that is coregistered with first pixel 71 is indicated by a six-pointed star. As part of the coregistering in step 35, the location of coregistered second pixel 72 has been adjusted from the preliminary location indicated by an asterisk. In this example, only the four closest first landmarks and the four associated second landmarks are used to coregister first pixel 71 to second pixel 72. The same coregistration procedure can be used, however, with fewer or more landmarks.

After first pixel 71 has been coregistered with second pixel 72, all remaining pixels of both first image object 63 and second image object 65 are coregistered with pixels inside or near the other image object using multiple first and second landmarks. Steps 29-35 are then repeated in order to coregister each image object with at least one other image object in another digital image. For example, where system 10 is coregistering image objects in digital images of tissue slices each containing five needle core tissue samples, ideally there should be five chains of coregistered image objects in which each object is coregistered with the two objects of the adjacent tissue slices except for the top and bottom slices, whose image objects are coregistered with only one other image object.

System 10 begins by coregistering that pair of image objects that exhibits the best fit according to the comparison factor and the object characteristics. Then the pair of image objects with the next best fit is coregistered. Once an image object has been coregistered with two other image objects, that image object can be removed from the pool of image objects that are compared to other image objects in step 29. The coregistration method continues by comparing an ever decreasing number of remaining image objects whose fit is increasingly less similar.

In step 36, first digital image 39 that includes first image object 63 and the second digital image that includes second image object 65 are displayed at the same time on graphical user interface 14. First digital image 39 depicts first tissue slice 20, and the second digital image depicts second tissue slice 22. First digital image 39 is displayed in a first frame, and the second digital image is displayed in a second frame. First pixel 71 is centered in the first frame and the coregistered second pixel 72 is centered in the second frame. A pixel is considered to be centered in a frame if the pixel appears to the user to be located in the middle of the frame, even if the pixel is not exactly centered. Similarly, where there are an even number of pixels across a frame, a pixel is considered to be centered if that pixel is adjacent to the location that is halfway between the sides of the frame.

In another embodiment, the first and second pixels 71-72 that are coregistered with each other are not centered in the first and second frames but rather are located at analogous positions in both frames. For example, first pixel 71 is positioned at a first reference location inside the first frame, and second pixel 72 is positioned at a second reference location inside the second frame such that the first reference location relative to the first frame corresponds to the second reference location relative to the second frame. First pixel 71 could be centered in the upper right quadrant of the first frame, and second pixel 72 would be centered in the upper right quadrant of the second frame.

Figure 11:
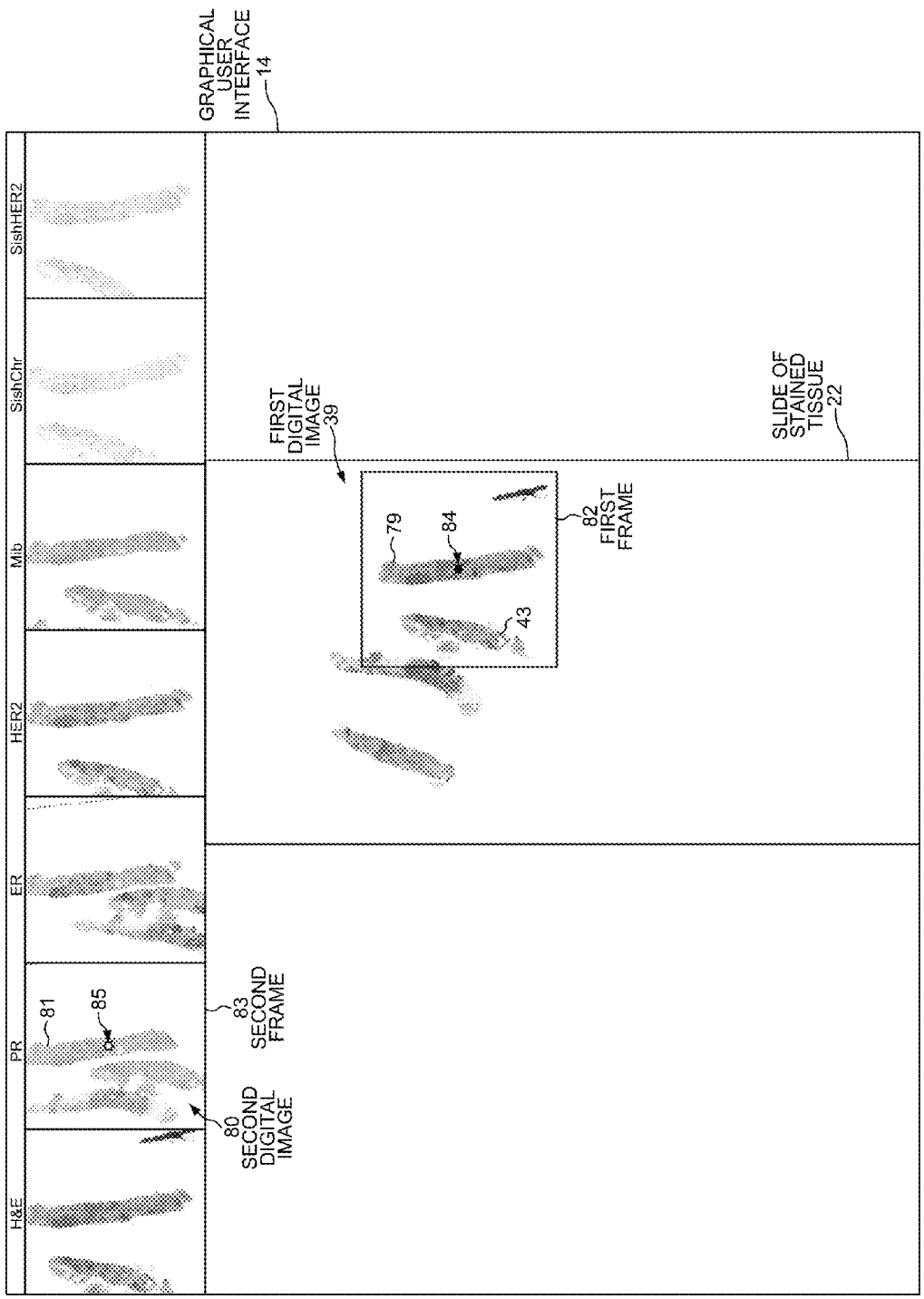
FIG. 11 is a screenshot of a graphical user interface of the system of FIG. 1 in which the center pixels in various frames are coregistered.

FIG. 11 is a screenshot of graphical user interface 14 of system 10 in step 36 of method 38. Both first digital image 39, including a first image object 79, and a second digital image 80, including a second image object 81, are displayed on the same screen. A portion of first digital image 39 is displayed in a first frame 82, and a portion of second digital image 80 is displayed in a second frame 83 on graphical user interface 14. First image object 79 includes a first pixel 84 that was coregistered in step 35 with a second pixel 85 in second image object 81. First pixel 84 is centered in first frame 82, and second pixel 85 is centered in second frame 83.

In step 37, system 10 shifts second digital image 80 within second frame 83 in response to a user shifting first digital image 39 relative to first frame 82 such that each pixel of second digital image 80 that is centered in second frame 83 always corresponds to a coregistered pixel of first digital image 39 that is centered in first frame 82. Thus, as a user of system 10 shifts first digital image 39 in relation to first frame 82, each pixel that is centered in the displayed portion of second digital image 80 corresponds to a coregistered pixel of first digital image 39 that is centered in first frame 82. The user of system 10 can shift first digital image 39 by clicking on any location in image 39 with a cursor and dragging image 39 while the mouse button remains depressed. The large rectangle in the main lower section of the screenshot of FIG. 11 represents first slide 21 of stained tissue.

Other digital images besides first digital image 39 and second digital image 80 are also displayed in frames in FIG. 11. The various digital images displayed in the row of frames along the top of graphical user interface 14 depict various tissue slices that have been stained with different biomarkers. Because the tissue slices are very thin, adjacent slices contain portions of the same tissue structures. The same tissue structures react differently to each different biomarker. The tissue slices depicted by the images in the top row of frames, from left to right, were stained with hematoxylin and eosin (H&E), progesterone receptor (PR) stain, estrogen receptor (ER) stain, human epidermal growth factor receptor 2 (Her2), Mib-1 antibody to Ki-67 antigen (Mib), silver in situ hybridization (SISH) for chromosome 17 detection (SishChr17), and silver in situ hybridization (SISH) for determination of HER2 gene status (SishHer2). Thus, second digital image 80 depicts a tissue slice stained with progesterone receptor (PR) stain. By centering the coregistered pixels showing the tissue structures that have been stained with different biomarkers, system 10 allows the user to obtain information on how the same tissue structures have reacted to different biomarkers. The pixels of the various digital images that are centered in each of the frames of the top row are coregistered with the pixel of first digital image 39 that is centered in first frame 82. While system 10 directly coregisters only pixels in digital images of adjacent tissue slices, the pixels in images of distant slices are indirectly coregistered through the chain of coregistered pixels in images of adjacent intervening slices. Thus, the center pixels in each of the frames of the top row are all directly or indirectly coregistered with one another.

Figure 12:
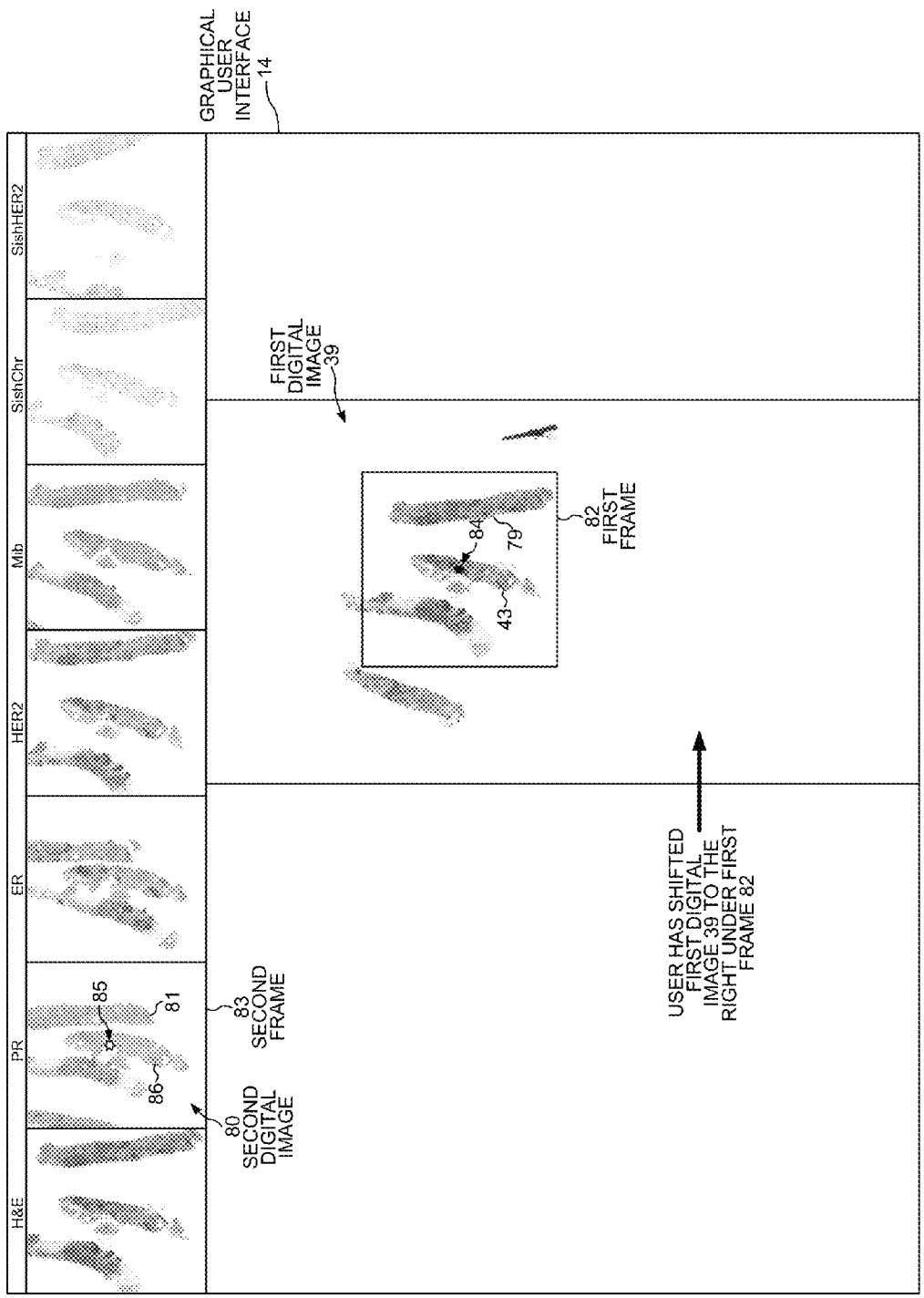
FIG. 12 is a screenshot of the graphical user interface of FIG. 11 in which a second digital image is shifted compared to its position in FIG. 11 as a user shifts a first digital image relative to a frame.

FIG. 12 illustrates how second digital image 80 is shifted compared to its position in FIG. 11 as the user shifts first digital image 39 relative to first frame 82. In FIG. 12, the user has shifted first digital image 39 to the right under first frame 82 such that a pixel 84 in image object 43 is in the center of first frame 82. System 10 has shifted second digital image 80 to the right such that a pixel 85 in an image object 86, which is coregistered with pixel 84, is centered in second frame 83. Note that second digital image 80 has been shifted less than the user shifted first digital image 39 because there is a larger distance between objects 79 and 43 in first digital image 39 than there is between objects 81 and 86 in second digital image 80.

Figure 13:
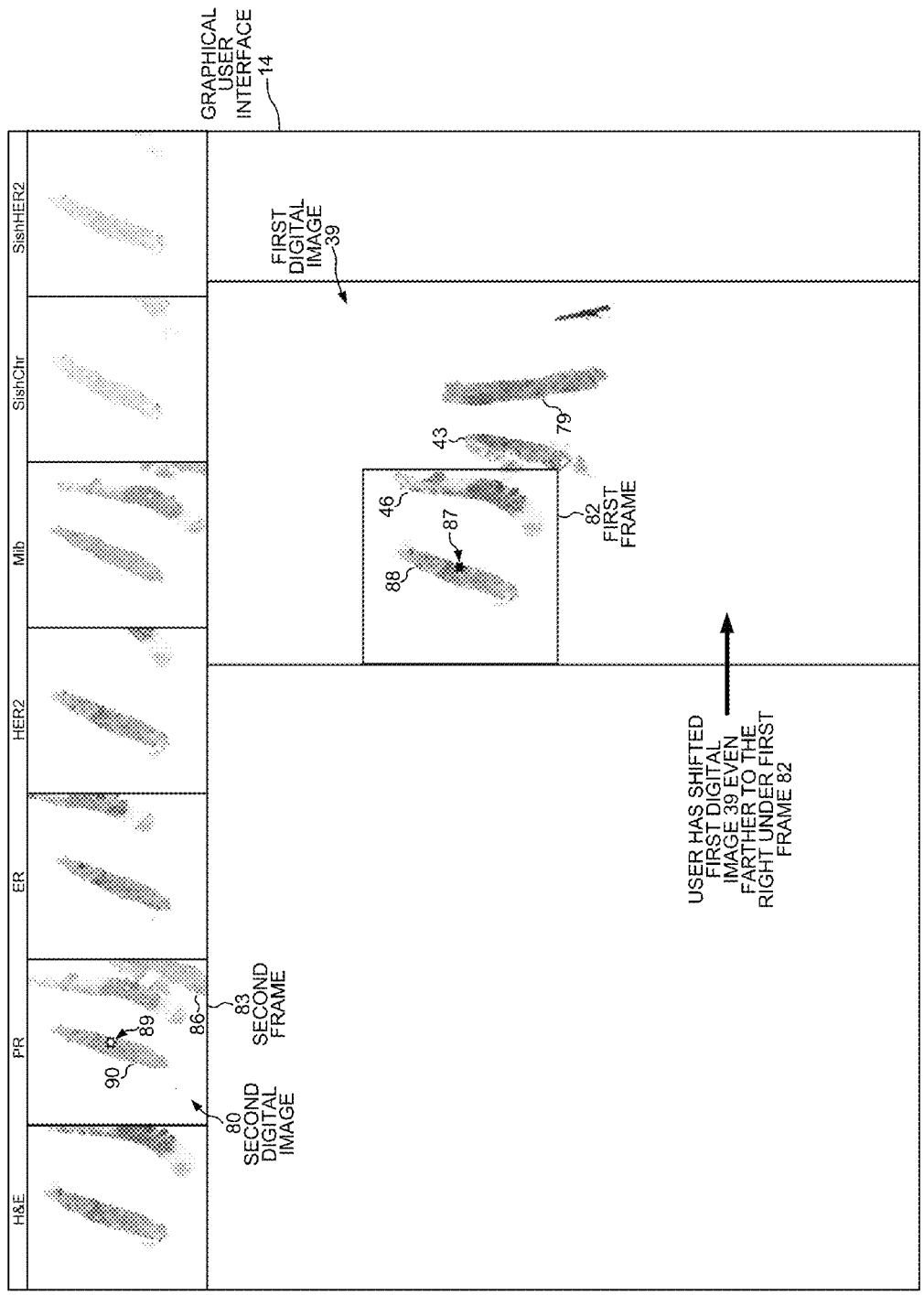
FIG. 13 is a screenshot of the graphical user interface of FIG. 11 in which the second digital image is shifted compared to its position in FIG. 12 as the user further shifts the first digital image relative to the frame.

FIG. 13 illustrates how second digital image 80 is shifted compared to its position in FIG. 12 as the user shifts first digital image 39 even farther to the right under first frame 82 such that a pixel 87 in an image object 88 is in the center of first frame 82. System 10 has shifted second digital image 80 to the right even farther such that a pixel 89 in an image object 90, which is coregistered with pixel 87, is centered in second frame 83.

In the embodiment of method 38 illustrated by FIGS. 11-13, the user shifts first digital image 39 under a stationary first frame 82. In another embodiment, however, the frame can be shifted over a stationary digital image. In that case, the second digital image 80 is shifted within second frame 83 in response to a user shifting first frame 82 over first digital image 39 such that each pixel of second digital image 80 that is centered in second frame 83 corresponds to a coregistered pixel of first digital image 39 that is centered in first frame 82.

Figure 14:
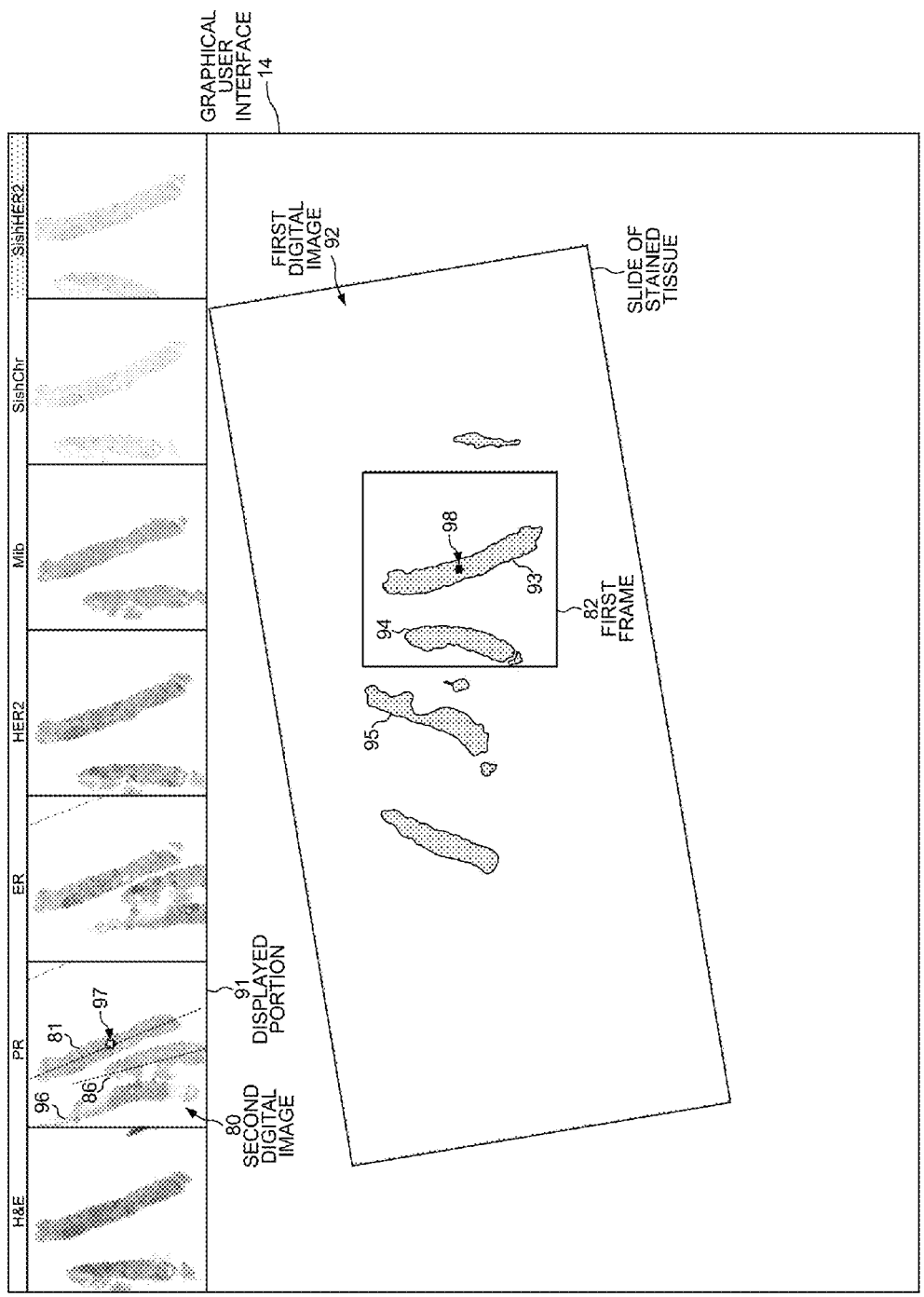
FIG. 14 is a screenshot of a graphical user interface showing that as a user shifts a first digital image relative to a frame, the pixels of a displayed portion of a second digital image are dynamically coregistered using only those landmarks in the second digital image that are associated with those landmarks in the first digital image that are located inside the frame.
Figure 15:
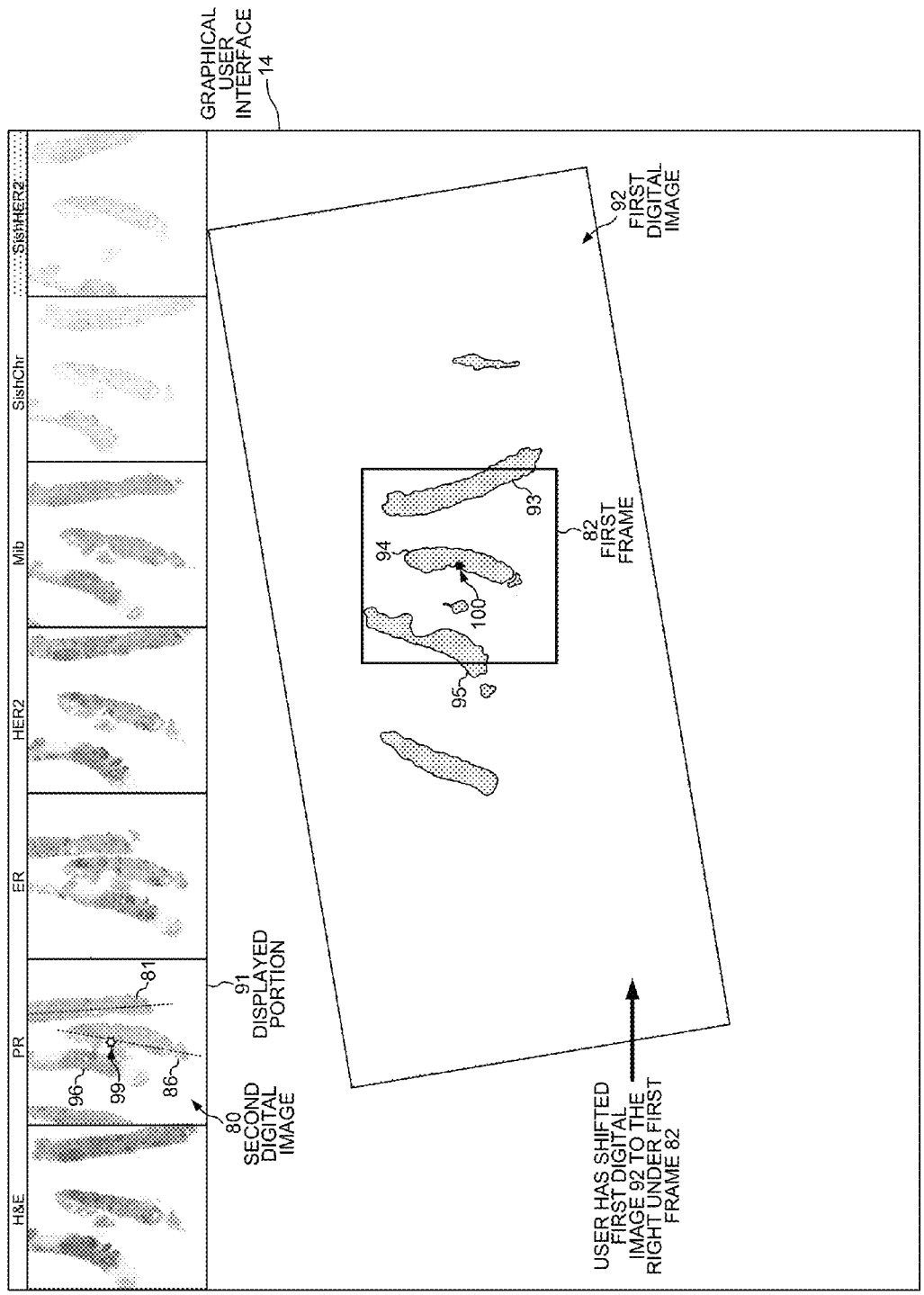
FIG. 15 is a screenshot of the graphical user interface of FIG. 14 in which the orientation of the displayed portion of the second digital image is changed as the user shifts the first digital image under the frame.

FIGS. 14-15 illustrate another aspect of method 38 in which the pixels of the displayed portion of a second digital image are dynamically coregistered as the user shifts a first digital image relative to a frame such that the pixel that is centered in the displayed portion is coregistered with the pixel that is centered in the frame using only those second landmarks in the second digital image that are associated with certain first landmarks in the first digital image that are located inside the frame. This dynamically updated coregistration has the effect of more closely aligning the image object that is centered in the displayed portion of the second digital image with the image object that is centered in the frame. Where landmarks associated with multiple image objects are used to coregister the pixels comprising the centered image objects, those centered image objects are oriented such that the weighted average orientation of the multiple image objects in the two digital images is optimized. However, where the coregistering of pixels in the second digital image uses only those second landmarks that are associated with first landmarks located on an image object in the frame over the first digital image, the image object that system 10 centers in the displayed portion of the second digital image becomes aligned with the image object that the user centers in the frame.

FIG. 14 is a screenshot of graphical user interface 14 of system 10 in the implementation of method 38 in which the pixels of a displayed portion 91 of second digital image 80 are coregistered with pixels of a first digital image 92 by using second landmarks in second image 80 that are associated with first landmarks in first image 92 that are both weighted based on their distances from the centers of frames. For example, the pixels of displayed portion 91 of second digital image 80 can be coregistered with the pixels of first digital image 92 by using only those second landmarks in second image 80 that are associated with first landmarks on an image object 93 in first frame 82 superimposed over first image 92. In FIG. 14, the pixels comprising the three image objects 93-95 in first image 92 are coregistered with the pixels comprising the three image objects 81, 86 and 96, respectively, in second image 80. As the user shifts first digital image 92, system 10 shifts displayed portion 91 of second digital image 80 so that each pixel that is centered in displayed portion 91 of second digital image 80 corresponds to a coregistered pixel of first digital image 92 that is centered in first frame 82. In FIG. 14, a pixel 97 that is centered in displayed portion 91 is coregistered with a pixel 98 that is centered in first frame 82. Because landmarks nearer to object 81 in image 80 and nearer to object 93 in image 92 are given a higher weighting in the coregistration of the two images, the orientation of object 81 in display portion 91 is similar to the orientation of object 93 in first frame 82. Only pixel 97 of second image 80 is exactly coregistered with pixel 98 of first image 92. The other pixels of second image 80 are rotated about pixel 97 to optimize the average coregistration of all pixels based on the weighted landmarks along the middle paths of the image objects 93 and 81.

FIG. 15 illustrates the changed orientation of second digital image 80 in displayed portion 91 as the user of system 10 shifts first digital image 92 from being centered on object 93 to being centered on object 94. The pixel 99 that is centered in displayed portion 91 of second digital image 80 corresponds to a coregistered pixel 100 of first digital image 92 that is centered in frame 82. In FIG. 15, system 10 has shifted and rotated displayed portion 91 of second digital image 80 in response to a user shifting first digital image 92 to the right relative to stationary first frame 82. The pixels of second image 80 within displayed portion 91 are rotated about pixel 99 to optimize the overall coregistration using landmarks on objects 94 and 86 that are weighted based on their distances from the centers of frame 82 and displayed portion 91. In one implementation, each coregistered pixel of second image 80 within displayed portion 91 is determined based only on those second landmarks on second image 80 that are associated with first landmarks on first image 92 that are located on image object 94. System 10 has shifted and rotated second image 80 such that the orientation of object 86 in displayed portion 91 coincides with the orientation of object 94 in frame 82.

In the embodiment of FIG. 15, only landmarks associated with image object 94 centered in frame 82 are used for coregistration. System 10 dynamically coregisters the pixels of displayed portion 91 of second image 80 as the user shifts first image 92 under frame 82 using only those second landmarks on second image 80 that are linked or associated with first landmarks on object 94 centered in frame 82. The coregistered image objects centered in displayed portion 91 and in frame 82 are aligned. In another embodiment, only landmarks inside frame 82 are used for coregistration.

In an additional embodiment, the user is able to zoom the first digital image in and out in the main lower section of graphical user interface 14. In FIG. 15, the entire first digital image 92 fits within the main lower section. In the additional embodiment, however, first image 92 can be expanded so that only a portion of first image 92 fits within the main lower section. But the size of first frame 82 remains the same. So as the user zooms in first image 92, a smaller portion of first image 92 fits within first frame 82. In the additional embodiment, system 10 dynamically coregisters the pixels of displayed portion 91 of second digital image 80 as the user zooms first digital image 92 within frame 82 such that pixel 99 that is centered in displayed portion 91 is coregistered with pixel 100 that is centered in frame 82 using only those second landmarks on image 80 that are associated with first landmarks on image 92 associated with the object shown in frame 82. As first image 92 is zoomed in, a greater proportion of the used landmarks are located on the image object that is centered in frame 82, which causes displayed portion 91 of second digital image 80 to become displayed in a coregistered orientation to how first digital image 92 is oriented in relation to the center of frame 82.

In FIGS. 11-13, the first digital image 39 in the main lower section of graphical user interface 14 depicts an unstained tissue sample, whereas the portions of the digital images shown in the row of frames at the top of graphical user interface 14 depict stained samples. In FIGS. 14-15, however, the first digital image 92 in the main lower section of graphical user interface 14 shows the entire image of a selected one of the digital images of stained tissue shown in the row of frames at the top. The user may select which image is displayed in the main lower section by clicking above the frame that contains the selected stained tissue. For example, in FIG. 14 the user has selected to display the digital image of tissue stained with Sish/HER2 in the main lower section, as indicated by the highlighted box above the SishHER2 frame. Thus, portions of the same image are displayed in the main lower section and in the upper right frame.

Figure 16:
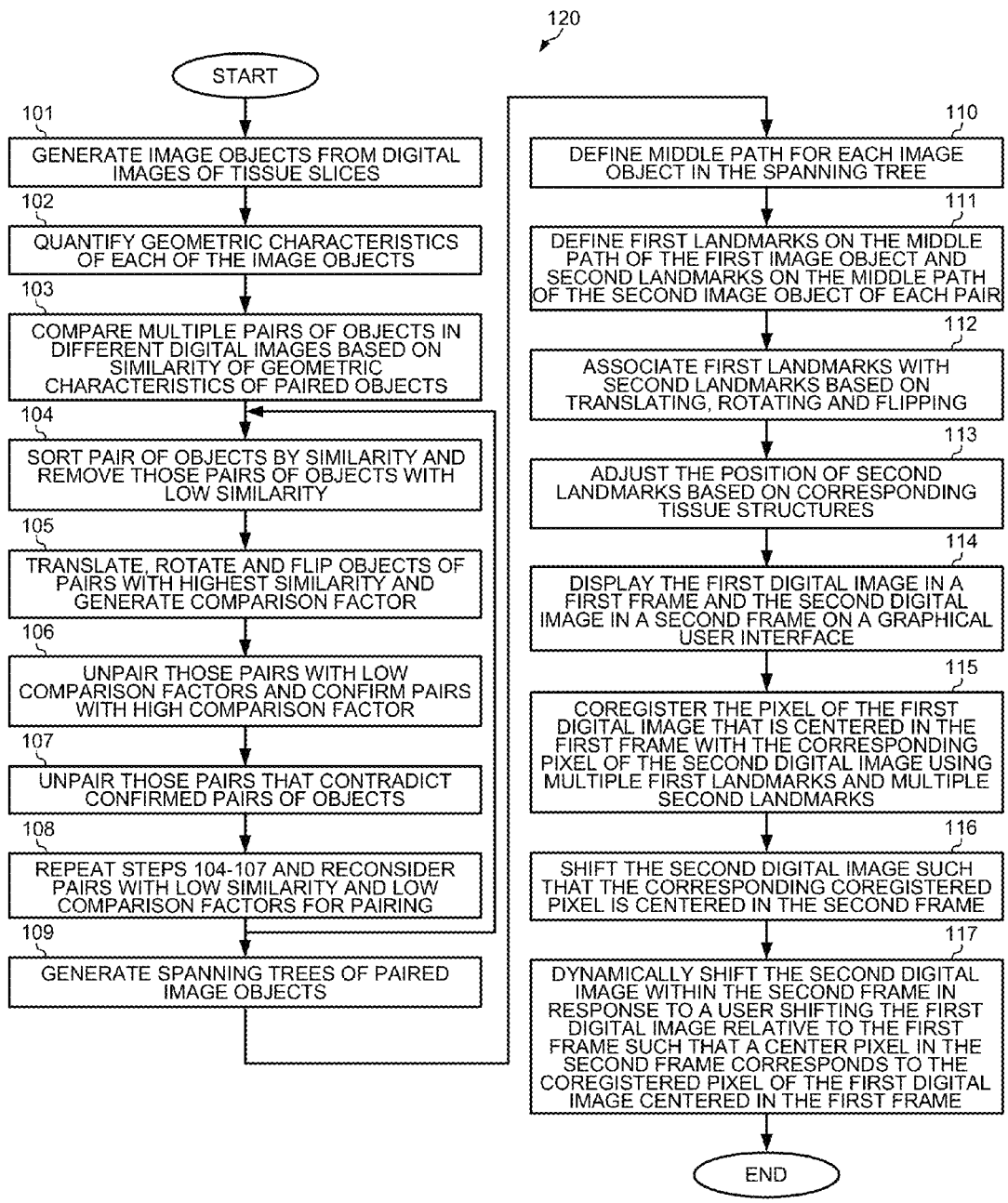
FIG. 16 is a flowchart of the steps of another method of coregistering digital images of tissue slices obtained from needle biopsies.

FIG. 16 is a flowchart of steps 101-117 of another method 120 for coregistering digital images of tissue slices obtained from needle biopsies. Method 120 involves detecting and segmenting tissue objects in the digital images, then detecting landmarks on the detected objects, and finally coregistering a pixel at a reference position in a first digital image with a corresponding pixel at the reference position in the second digital image based on multiple landmarks in both images. In step 101, system 10 generates image objects from the digital images of the needle biopsies. Overlapping and touching image objects must be separated before the image objects can be compared with similar image objects in other digital images. Combined image objects are separated based on the linearity of the objects.

Figure 17A:
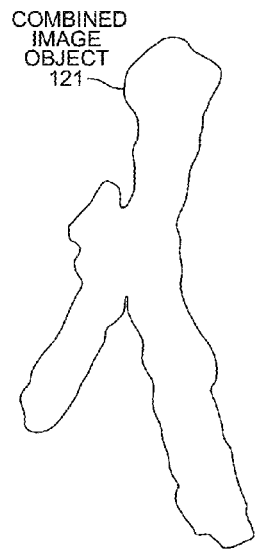
FIGS. 17A-F illustrate another way of separating image objects of tissue samples that are in contact with or overlap each other.
Figure 17B:
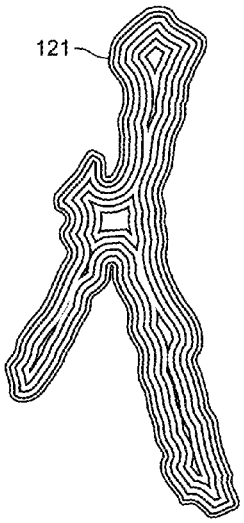
Figure 17C:
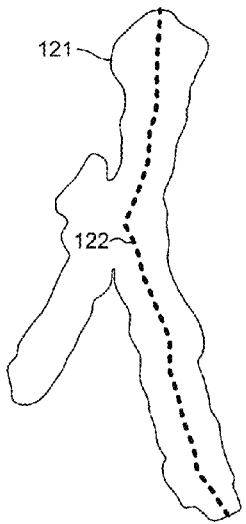
Figure 17D:
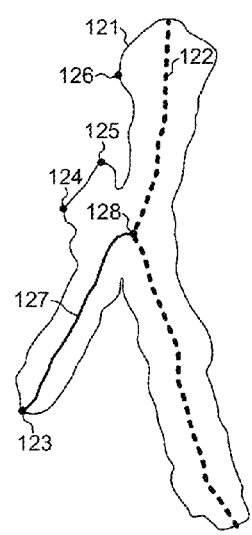

FIGS. 17A-F illustrate one way of separating image objects of tissue samples that are in contact with or that overlap each other. First, image objects with a low linearity are identified. An object has a low linearity when it has a large ratio between its maximum middle path width to its median middle path width. FIG. 17A shows a combined image object 121 that will be separated into its constituent tissue samples using concave points. Combined image object 121 is identified as an object with a low linearity. FIGS. 17A-C illustrate the process by which system 10 determines the middle path width of the combined image object 121. A middle path 122 traverses through image object 121 along a path that is equidistant from opposite sides of the object. The route of middle path 122 is determined by incrementally shrinking object 121 by the same small steps from all sides, as shown in FIG. 17B. Where the two shrinking sides meet is the route of the middle path. Where there are multiple branches of the middle path, the longest single path is used. The middle path width is determined by detecting the endpoints on the boundary of the object that are the farthest away from each other. There is an endpoint at the end of each branch of an object. Two of the endpoints are at the ends of the middle path. A middle path width is determined for each of the remaining endpoints 123-126. The maximum middle path width is the distance from the middle path to farthest endpoint. For an endpoint 123 on the boundary of object 121, as indicated in FIG. 17D, the middle path width is the distance between endpoint 123 and middle path 122 along the middle path of the branch, i.e., the length of branch middle path 127 between endpoint 123 and point 128 on middle path 122. The maximum middle path width and the median middle path width are determined based on the widths for each of the endpoints at the ends of the branches of the object.

Figure 17E:
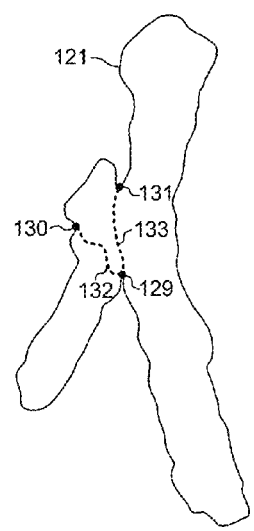
Figure 17F:
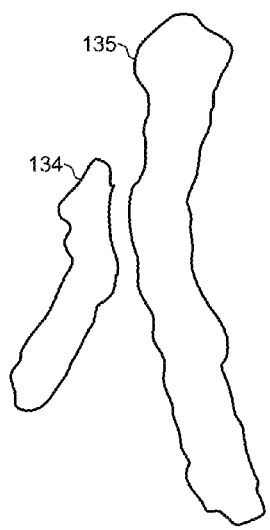
Figure 21:
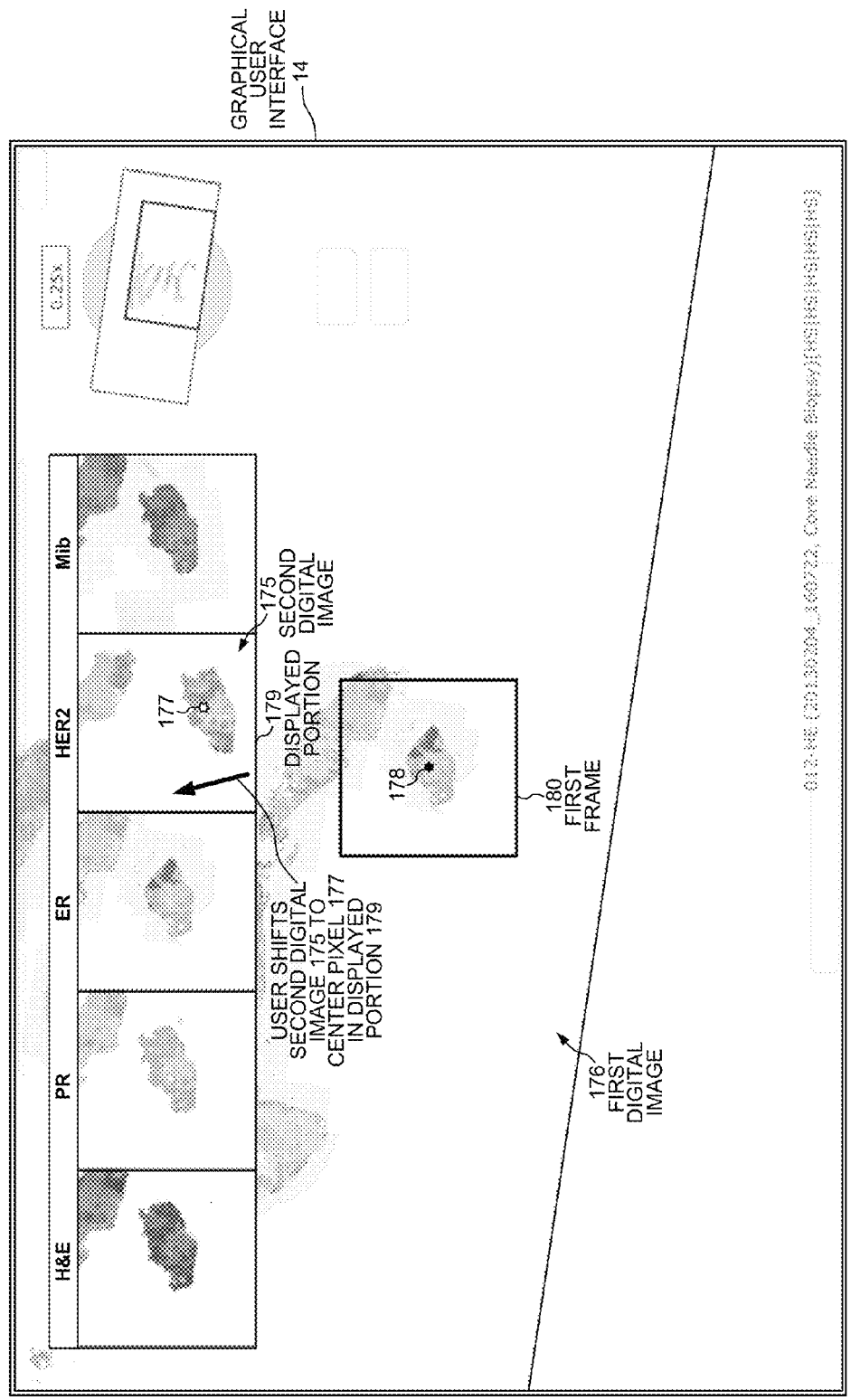
FIGS. 21-22 are screenshots of the graphical user interface of the system of FIG. 1 illustrating how the coregistration of two images is manually adjusted by shifting the displayed portion of a second image.

For those objects having a low linearity, such as combined object 121, points are identified at the center of concave curves along the boundary. Some of the concave points 129-131 on the boundary of combined object 121 are shown in FIG. 17E. The combined image object is then split into smaller objects along splitting paths that connect the concave points. A splitting path is defined as the path between two concave points that minimizes the cumulated sum of the inverse intensities of the pixels along the path. Thus, the splitting path follows pixel intensity. For example, splitting path 132 connects concave points 129 and 130, and splitting path 133 connects concave points 129 and 131. Finally, only those split smaller objects of a combined object are retained that significantly (>10%) increase the combined linearity of the split portions in comparison to the linearity of the combined object. For example, splitting path 132 does not result in two split portions having a greater combined linearity and is therefore rejected. On the other hand, splitting path 133 results in two split portions having the greatest combined linearity and is therefore kept. FIG. 17F shows combined image object 121 after it has been split into the two split portions 134-135 that have the greatest combined linearity. Split portions 134-135 are formed by separating object 121 along splitting path 133 that connects concave points 129 and 131. Split portions 134-135 are logically split in data network 40 and are treated as separate image objects for purposes of coregistration, but the digital image is not altered by separating split portions 134-135 in the image.

FIGS. 18A-D illustrate a way to separate another type of combined object that is curved instead of having branches. FIG. 18A shows a curved combined object 137 and its middle path 138. Combined image object 137 is separated into its constituent tissue samples using a single concave point 139 on the boundary and a nearby point 140 at the highest local curvature on middle path 138, as shown in FIG. 18B. Whereas the low linearity of combined image object 121 was determined by the large ratio of its maximum middle path width to its median middle path width, the low linearity of combined image object 137 is determined by its high angle of curvature. The angle of curvature is defined as the ratio of the Euclidean distance 141 between the two endpoints 142 and 143 of middle path 138 and the length of middle path 138 between endpoints 142-143. A linear object has a ratio of one; combined image object 137 has a low ratio.

In order to split combined image object 137 into more linear objects, a third point 144 is defined at the intersection between the boundary of combined object 137 and the line 145 intersecting concave point 139 and point 140 on middle path 138. FIG. 18B shows that point 140 is at the location of the highest local curvature along middle path 138.

FIG. 18C shows that combined image object 137 is split into smaller objects along a splitting path 146 that connects concave point 139 to the intersecting point 144. The splitting path need not be linear but can follow a boundary of intensity change in the pixels. FIG. 18D shows combined image object 137 after being split along splitting path 146 into two split portions 147-148. Split portions 147-148 are logically split in data network 40 and treated as separate image objects for purposes of coregistration, but the digital image of the tissue sample is not altered by separating split portions 147-148 in the image.

Image objects are generated in each of the digital images taken of each slice of the paraffin-embedded tissue samples. Each image object is linked to pixels in data network 40.

In step 102, characteristics such as length, width, area and shape index of the image objects are quantified for each of the image objects in each of the digital images. One shape index represents how well an image object fits into a square of similar size. Another shape index is calculated by dividing the border length of the object by the square root of its area.

In step 103, pairs of objects from among all of the images are compared based on the similarity of geometric characteristics of the paired objects. Each possible pair of objects from among all of the images is characterized by a similarity measure, which is the inverse of the sum of the absolute differences of the geometric characteristics of the two objects. For example, in a scenario of four digital images each containing five image objects, there are one hundred fifty possible pairs of image objects to compare. System 10 also tests whether merging one of the two image objects with an adjacent image object would yield a higher similarity to the other image object than without merging. If so, the similarity between the merged image object and the other image object is also stored together with a mark indicating the necessity of merging. Pairs of image objects with a similarity measure below a fixed threshold are unpaired.

In step 104, pairs of objects are sorted by similarity, and those pairs with low similarity are removed from the ranking. Pairs of objects are ordered with respect to the similarity measure that is defined in step 103. This includes the similarity obtained from merging one of the two objects as described above. The order of similarity is descending, with pairs of higher similarity ranked higher than those with lower similarity.

In step 105, a comparison factor is calculated for each pair ranked in step 104 in order of the similarity. If a pair has been marked for merging in step 27, the same merging in step 105 is performed before the comparison factor is computed. The value of the comparison factor is then stored for all objects. In one implementation, the comparison factor is an overlap ratio. One way of calculating the overlap ratio is to divide the number of pixels that overlap by the total number of pixels of the combined superimposed image objects. One of the objects of each pair is translated, rotated and/or flipped in order to achieve the highest comparison factor with its paired object.

In step 106, system 10 then confirms each pair whose comparison factor is above a predetermined threshold and unpairs those pairs whose comparison factor is below the threshold. In step 107, those pairs that conflict with the pairing of previously confirmed object pairs are unpaired. For example, a pairing of objects is unpaired that includes an object from another pair with a higher similarity as defined in step 103 and that has already been confirmed based on its comparison factor.

In step 108, steps 104-107 are repeated with lower thresholds to ensure that each digital image has at least one image object that is paired with another image object in another digital image. In step 108, lower values for the thresholds for similarity and for the comparison factor are used in the comparison of objects that have been unpaired in steps 104-107 because of low similarity or low comparison factor. Two objects are directly associated if they form a pair by the end of the steps 104-107. Two objects are indirectly associated if they do not form a pair by the end of the first iteration of steps 104-107 but their association can be deduced through their association with other paired image objects. The association process is transitive in that if a first object in a first image is paired with a second object in a second image, and that second object in the second image is paired with a third object in a third image, then the first object in the first image is indirectly associated with the third object in the third image. In this example, the first and second objects and the second and third objects would be paired in steps 104-107 because of their high similarity and comparison factors. On the other hand, the first object and the third object would be unpaired because they have either a low similarity or a low comparison factor.

In step 109, spanning trees of image objects are generated from the pairs identified in steps 103-108. The vertices of the trees are the image objects from the different tissue slices. For example, if five needle core samples are taken of a patient, and the paraffin-embedded tissue samples is sliced into twenty slices, then there are one hundred image objects from which five spanning trees of twenty coregistered objects are generated. An edge is defined between two image objects at the vertices of the spanning tree if the two objects are directly paired. A weight is assigned to each edge of the tree as the inverse of the comparison factor between the image objects linked by the edge. In one implementation, the weight of an edge between two image objects is the inverse of the overlap ratio between the two image objects.

The spanning tree is a connected and undirected graph for which all of the vertices (image objects) lie in the tree and which contains no closed loops. For example, a spanning tree between objects in four slices can include the following pairs: object 1 in slice 1 paired with object 2 in slice 2; object 2 in slice 2 paired with object 3 in slice 3; and object 3 in slice 3 paired with object 4 in slice 4. The spanning tree could alternatively include the following pairs: object 1 in slice 1 paired with object2 in slice 2; object 1 in slice 1 paired with object 3 in slice 3; and object 2 in slice 2 paired with object 4 in slice 4. In the optimal implementation of method 120, the weights of the edges between vertices of the spanning tree are minimized. Thus, the cumulated sum of the inverse of the comparison factors between image objects that are paired is minimized.

In step 110, a middle path is defined through each of the objects in the spanning tree defined in step 109. The process by which system 10 defines middle paths through objects is the same as in step 31 of method 38.

In step 111, landmarks are placed on the middle path of one image object of each pair of image objects in the spanning tree. First, the middle of the middle path is determined, and a center landmark is placed at the middle of middle path. Then, additional landmarks are placed on the middle path at constant intervals on either side of the center landmark. In one implemetation, landmarks are placed only on the middle path. In another implementation, additional landmarks are placed at locations that are not on the middle path but rather on a corrected middle path. FIGS. 19A-B illustrate how additional landmarks are placed on corrected middle paths. FIG. 19A shows an image object 150 with a middle path 151. FIG. 19B shows a paired image object 152 with a middle path 153. The tops of the image objects have been distorted, which has caused middle paths 151 and 153 to deviate from the optimal middle path towards the tops of the image objects.

Middle path 151 is corrected by extending the path in a local direction 154 from a source point 155 on middle path 151. Source point 155 is determined based on its distance from the endpoint of middle path 151. The distance from the endpoint depends on the median middle path width of image object 150. The corrected middle path is defined by a new endpoint 156 located at the intersection of the boundary of image object 150 and the extended local direction 154. Although not illustrated in FIG. 19A, middle path 151 would also be corrected near its lower endpoint.

The landmarks that are placed at constant intervals along middle path 151 are placed on the corrected middle path. These additional landmarks are located inside of the boundary of the image object. For example, the average linear direction of the top fifth of middle path 151 can be extended towards the upper boundary of image object 150, and an additional landmark 157 can be placed at an appropriate interval from the last landmark along the extension line instead of along the original middle path 151. Extending the path on which landmarks are placed near an object boundary based on the local direction of the middle path also reduces the imprecision caused by defining the path to be equidistant from "opposite" boundaries as that path approaches the boundary. In FIG. 19B, an additional landmark 159 is also placed at the appropriate interval from the last landmark along an extension line 160 instead of along the original middle path 153. The additional landmarks 157 and 159 improve the coregistration of image objects 150 and 152.

In step 112, landmarks are placed on the middle path of the second image object of each pair of objects. The second landmarks on the middle path of the second object are associated with first landmarks on the middle path of the first object by translating, rotating and flipping the second object to achieve the best overlap with the first object. The second landmarks are then placed on the middle path of the second object at locations associated with the locations of the first landmarks on the first object. Second landmarks are associated with their corresponding first landmarks based on their distances to the transformed first landmarks. The transformation is defined by the translation, rotation, and flip parameters that were computed in step 105 to maximize the comparison factor between the two image objects. Each landmark in the first image object and in the second image object includes an orientation vector representing the local direction of the middle path at the landmark.

In another embodiment, the landmarks on the middle path of the second image object are defined as those points in the middle that minimize the distance to the transformed landmark points of the first image object. The transformation is defined by the translation, rotation and flip parameters that were computed in step 105 to maximize the comparison factor between the two image objects.

In step 113, the positions of the second landmarks are adjusted based on corresponding tissue structures in the first and second image objects. The image objects are segmented and classified to generate many subobjects that correspond to higher order tissue structures, such as stromal tissue regions, fatty tissue regions, cancerous regions and connective tissue regions. Thus, there are several hierarchical levels in data network 40 between the first image objects 41 shown in FIG. 5 and the pixels 42. Data network 40 also includes a hierarchical branch representing image objects in the second digital image, which in turn includes multiple hierarchical levels. System 10 defines a first neighborhood around each first landmark and adjusts the position and the orientation vector of the associated second landmark so that the higher order tissue structures in the first neighborhood coincide with the higher order tissue structures in the second neighborhood around the second landmark. The two neighborhoods have the same shape and size. In one implementation, these two neighborhoods are circles centered on the two landmarks. The first neighborhood is static in the first digital image because the position of the first landmark is fixed. The second neighborhood moves within the second digital image because the position of the second landmark is adjusted.

In step 114, a first digital image that includes a first image object and a second digital image that includes a second image object are displayed at the same time on graphical user interface 14. The first digital image depicts a first tissue slice, and the second digital image depicts a second tissue slice. The first digital image is displayed in a first frame, and the second digital image is displayed in a second frame.

In step 115, pixel-to-pixel registration is performed in real time as the user is viewing graphical user interface 14 based on the pixel that is at the center of the first frame in the first digital image. The pixel at the center of the first frame is denoted as the centered pixel in the following description. The centered pixel is coregistered with a second pixel in the second digital image using multiple first landmarks in the first digital image and multiple second landmarks in the second digital image.

FIG. 20 illustrates the procedure for coregistering the second pixel 161 with the centered pixel 162. In this example, for clarity purposes only the four closest first landmarks in the first image and the four associated second landmarks in the second image are used to coregister second pixel 161 with centered pixel 162. First, a virtual first landmark 163 is generated. The position of first virtual landmark 163 is a weighted mean of the positions of the landmarks 165-168 in the first digital image. The orientation vector 164 of first virtual landmark 163 is a weighted mean of the local middle path directions at each of the landmarks 165-168. The weights are computed by using the inverse distance of each landmark to first pixel 162. Second, the position and orientation vector 169 of a second virtual landmark 170 is analogously computed as a weighted mean of the positions and orientation vectors of the second landmarks 171-174 using the weights of the respective first landmarks. The difference in the orientation vector of the first virtual landmark 163 to the orientation vector of the second virtual landmark 170 is used to determine the position of second pixel 161. Second pixel 161 is shifted by the angle between the orientation vector of the first virtual landmark and the orientation vector of the second virtual landmark. Second pixel 161 is assigned the weighted orientation vector 169 of the second landmarks 171-174. After second pixel 161 has been coregistered with centered pixel 162, the associated pixels in the remaining other digital images are coregistered with centered pixel 162. For each pixel that is to be coregistered with centered pixel 162, an additional virtual landmark is determined using second landmarks in the other digital image with the weights of the corresponding first landmarks.

In step 116, the second digital image is shifted such that the corresponding coregistered second pixel 161 is centered in the second frame. Thus, centered pixel 162 is displayed in the center of the first frame, and coregistered second pixel 161 is displayed at the center of the second frame. In addition, the second digital image is rotated in the second frame about the second pixel 161 based on the orientation vector 164 of centered pixel 162. Thus, a second image object with a middle path passing through second landmarks 171-174 is rotated so as to become aligned with a first image object with a middle path passing through first landmarks 165-168.

Pixels in other digital images can also be coregistered with centered pixel 162 in the first digital image. In that case, the pixels that are coregistered with centered pixel 162 at the center of the first frame are centered in their respective frames. Moreover, the respective digital images are rotated about the coregistered pixels in order to align with the orientation vector 164 of centered pixel 162

In another embodiment, "centered" pixel 162 and second pixel 161 are coregistered with each other, but are not centered in the first and second frames. Rather, pixels 161-162 are located at analogous positions in both frames. For example, if pixel 162 is positioned at a first reference location inside the first frame, then second pixel 161 is positioned at a second reference location inside the second frame such that the first reference location relative to the first frame corresponds to the second reference location relative to the second frame. Pixel 162 could be centered in the upper left quadrant of the first frame, and second pixel 161 would be centered in the upper left quadrant of the second frame. Additional coregistered images would be positioned analogously.

In step 117, the second digital image is dynamically shifted within the second frame in response to the user of system 10 shifting the first digital image relative to the first frame. The new second pixel in the second frame corresponds to a coregistered pixel in the first digital image that has become centered in the first frame. In addition, the second digital image is rotated about the new second pixel such that the orientation of the second digital image corresponds to the orientation vector of the first virtual landmark used to coregister the pixels.

FIGS. 21-24 illustrate a manual procedure for adjusting the coregistration of a second digital image 175 with a first digital image 176 after the digital images have been displayed on graphical user interface 14 in step 36 of method 38 or in step 114 of method 120. Second digital image 175 can be manually shifted by clicking on the image and holding a mouse button depressed while the user moves the computer mouse. The location of a particular second pixel 177 can be coregistered with the location of centered pixel 178 by shifting second pixel 177 to the center of the displayed portion 179 of second digital image 175. The user of system 10 finds the second pixel 177 that corresponds to centered pixel 178 based on the visual observation of similar tissue structures in both the second and first digital images 175-176.

Figure 22:
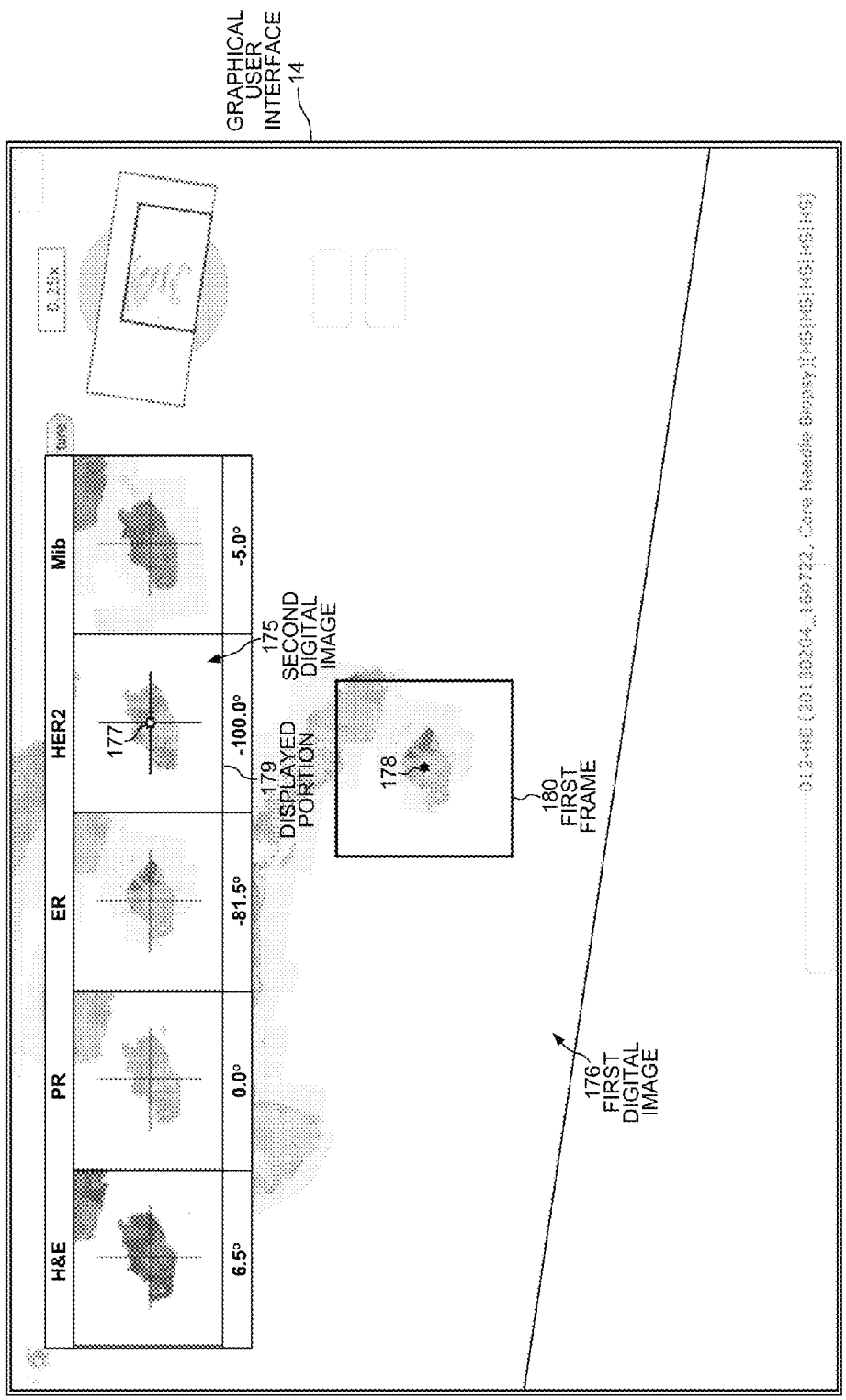

FIG. 22 shows second digital image 175 after it has been shifted within displayed portion 179 such that second pixel 177 is centered in displayed portion 179. FIG. 22 also lists the degrees by which the images in the row of frames were rotated so as to become coregistered with first digital image 176. For example, second digital image 175 was rotated by −100.0 degrees such that the image objects in second digital image 175 have become aligned with image objects in first digital image 176. FIG. 22 shows centered pixel 178 centered in the middle of a first frame 180. In another embodiment, centered pixel 178 is located at a location that is designated by markings on graphical user interface 14 other than a frame. For example, centered pixel 178 could be located at the center of a circle or oval. Alternatively, pixel 178 could be located in graphical user interface 14 at the intersection of cross hairs in a manner similar to how pixel 177 is located in displayed portion 179 at the intersection of cross hairs.

The procedure for manually adjusting the coregistration of second digital image 175 with first digital image 176 involves selecting a second digital image to be adjusted, shifting the second digital image based on user input while the first digital image does not move relative to the first frame, and then coregistering the first pixel at the first reference location with a third pixel that is positioned at the second reference location as a result of the shifting.

The locations of the pixels whose coregistration is manually adjusted can be defined as landmarks. The procedure for manually adjusting the coregistration of pixels becomes the manual modification of landmarks. The first and second digital images need not be displayed at the same magnification. Thus, the user selects the magnification and the region in the images that is to be displayed in the frames. System 10 is then switched into the correction mode. Those images in the row of frames that the user wishes to adjust are individually shifted in such a way that the image regions displayed within the individual frames appear to the user with improved regional similarity. The user then locks in the manual changes made to the positions of the images, and the system exits the correction mode. New landmarks have been automatically added to the shifted images at the reference locations where the pixels were manually coregistered. Pixels in the vicinity of the new landmark are now coregistered using multiple landmarks in which the closest landmarks, including the new landmark, are given greater weights.

Figure 23:
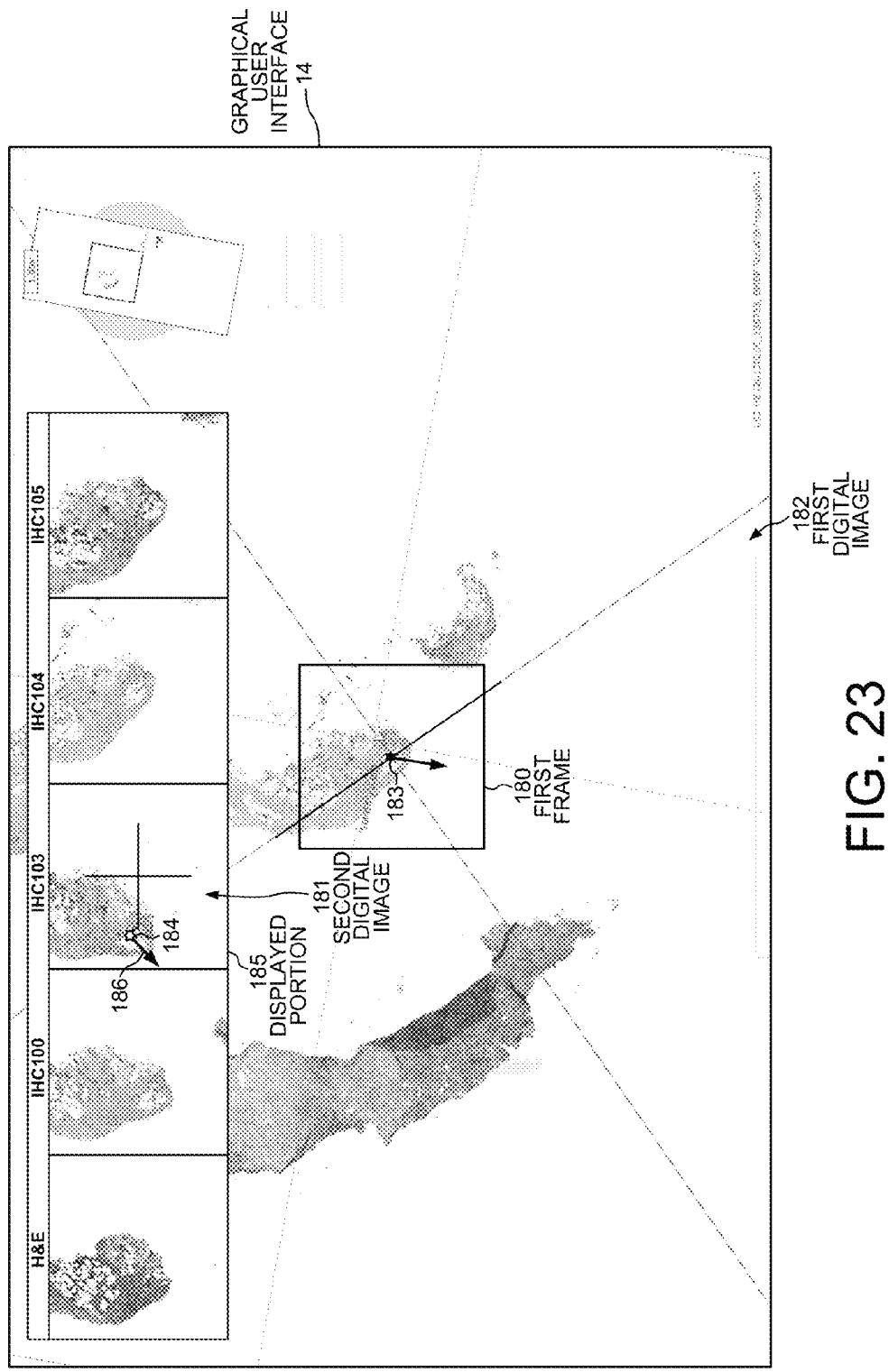
FIGS. 23-24 are screenshots of the graphical user interface of the system of FIG. 1 illustrating how the coregistration of two images is manually adjusted by shifting and rotating a second image.
Figure 24:
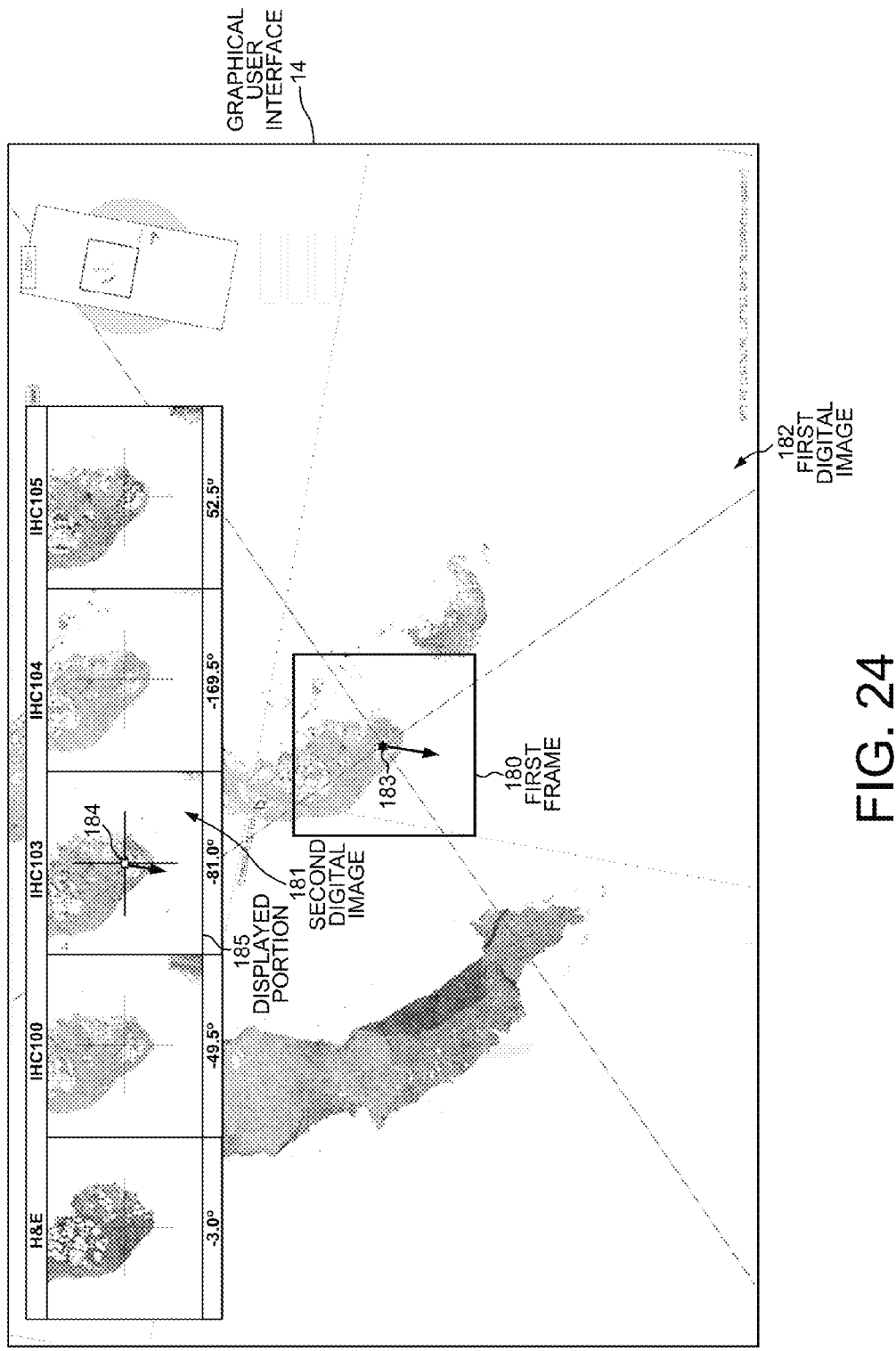

FIGS. 23-24 illustrate the procedure for manually adjusting the coregistration of a second digital image 181 with a first digital image 182 by selecting the second digital image to be adjusted, both shifting and rotating the second digital image based on user input while the first digital image does not move relative to the first frame 180, and then coregistering the second digital image 181 with the first digital image 182 as the second digital image is positioned after the shifting and rotating.

FIG. 24 shows that third pixel 184 has been shifted to the center of displayed portion 185 of second digital image 181. Although displayed portion 185 is enclosed in a frame in FIG. 24, in other embodiments the displayed portion of second digital image has an irregular shape, and third pixel 184 is shifted to a reference location designated by markings such as cross hairs. The manual shifting of second digital image 181 coregisters third pixel 184 with first pixel 183. First pixel 183 is located at the first reference location, and third pixel 184 is positioned at the second reference location. In this example, both the first and second reference locations are at the centers of square frames. In other embodiments, the reference locations are located at corresponding locations in other shaped frames. For example, both reference locations could be located at the left focal points of ellipsoid frames. In another example, both reference locations could be located at the centers of the lower left quadrants of rectangular frames.

In addition to coregistering third pixel 184 with first pixel 183, second digital image 181 is also rotated about third pixel 184 such that second digital image 181 is coregistered with first digital image 182. The image objects in second digital image 181 that are visible in displayed portion 185 become aligned with the corresponding image objects in first digital image 182. Thus, system 10 allows the user to shift and rotate individual second images so as to modify the registration of the displayed regions of the images to improve the regional similarities of the displayed images.

In FIGS. 23-24, system 10 has added new landmarks to first and second digital images 182-181 where the pixels 184-183 were manually coregistered. The arrows emanating from pixels 183-184 represent the orientation vectors of the new landmarks. For example, the orientation vector 186 emanating from third pixel 184 is a weighted mean of the local middle path directions the other landmarks located on the middle path of the image object shown in displayed portion 185. The orientation vectors of the two new landmarks have been aligned in FIG. 24, which signifies that the image object that is visible in displayed portion 185 has been aligned with the corresponding image objects in first digital image 182 based on the middle paths of the two objects. The −81.0 degrees listed below displayed portion 185 indicates that second digital image 181 has been rotated by −81.0 degrees compared to its original orientation. Part of the −81.0 degree rotation was performed automatically by system 10, and part of the −81.0 degree rotation (e.g., −35 degrees) was performed by manual adjustment by the user.

Data analysis server 13 includes a computer-readable storage medium having program instructions thereon for performing method 38. Such a computer-readable storage medium can include instructions for generating image objects in digital images and for coregistering associated pixels in different digital images.

System 10 for coregistering images of tissue slices can also improve upon the quality of the initial coregistration based on user interaction that is performed for other purposes. One of the uses of system 10 is to quantitatively evaluate tissue structures in the digital images of stained tissue slices. The image analysis program of system 10 classifies and segments image objects in the images and then measures, counts and categorizes those image objects. For example, a pathologist may outline the boundaries of tumor regions on consecutive tissue slices in order to determine the volume of the tumor. Or a pathologist may wish to obtain a grade or score of a stained tissue sample in order to determine the progress of a disease or the effects of medication. Examples of such a histopathological score include a Gleason score, an Allred score, an Elston-Ellis score, an Her2 score, and a HercepTest score. However, it is typically not computationally feasible to perform segmentation on all of the tissue structures in a digital image of stained tissue. Segmenting all of the image objects would be too computationally intensive because digital images of tissue slices typically have a very high spatial resolution, which can be on the order of several Giga-pixels. Therefore, pathologists typically annotate the digital images of tissue slices by designating regions of interest and restrict the image analysis to those regions.

Limiting the image analysis to the designated regions of interest also improves the quality of the quantitative evaluation because the analysis is not performed on artifacts and boundary regions of the tissue slides, which would skew the counting and measurements used for the analysis. For each differently stained tissue slice of a tissue sample, the pathologist typically marks multiple regions of interest that are to be analyzed. System 10 improves the coregistration between the digital images of adjacent tissue slices using the input from the pathologist that designates the regions of interest. The need to perform the separate step of updating landmarks to improve the coregistration at local areas of non-linear deformation of adjacent tissue slices is thereby avoided.

FIGS. 25-31 illustrate the steps of a method for improving the coregistration of a first digital image 187 with a second digital image 188 after the digital images have been displayed on graphical user interface 14 in step 36 of method 38 or in step 114 of method 120. The method for improving coregistration, however, can be performed on images of any kind of stained tissues, not just on images from samples of needle biopsies. The method is particularly applicable to the coregistration of local areas of non-rigid deformations on whole slide images. The digital images 187-188 depict adjacent z slices taken from a tissue sample at corresponding positions in the x and y dimensions. In this example, the first tissue slice is stained with estrogen receptor (ER) stain, and the second tissue slice is stained with Human Epidermal growth factor Receptor 2 (Her2). The graphical user interface 14 also displays a third digital image of a tissue slice that is stained with progesterone receptor (PR) stain. Portions of the same anatomical object are stained in different ways by the various stains as shown in the three digital images that are displayed at the same time on graphical user interface 14.

Figure 25:
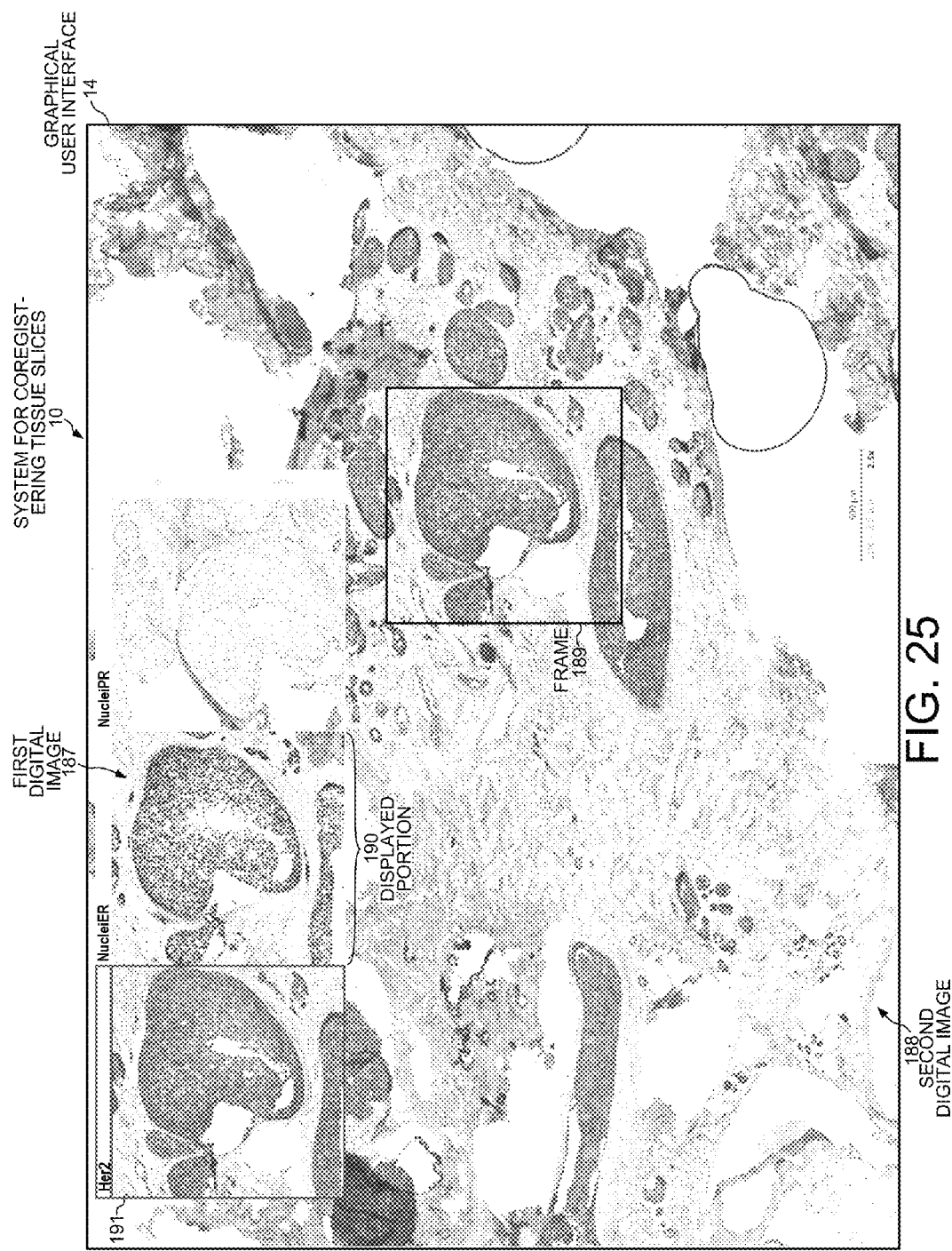
FIG. 25 illustrates a step in a method for improving coregistration in which a digital image of a tissue slice is displayed such that an area of the image is enclosed by a frame.

FIG. 25 shows second digital image 188 of a second tissue slice displayed on graphical user interface 14 such that an area of image 188 is enclosed by a frame 189. The displayed portion of second digital image 188 is larger than the frame 189. Only a portion 190 of first digital image 187 of a first tissue slice is displayed on graphical user interface 14. The displayed portion 190 of first digital image 187 has the shape of frame 189. Thus, the area of second digital image 188 that is enclosed by frame 189 corresponds to the displayed portion 190 of first digital image 187. At the step of the method shown in FIG. 25, system 10 has already coarsely coregistered the area of second digital image 188 that is enclosed by frame 189 with the displayed portion 190 of first digital image 187. The area of second digital image 188 that is enclosed by frame 189 is also reproduced inside a second frame 191 that is located next to portion 190 in the row of frames along the top of graphical user interface 14.

Figure 26:
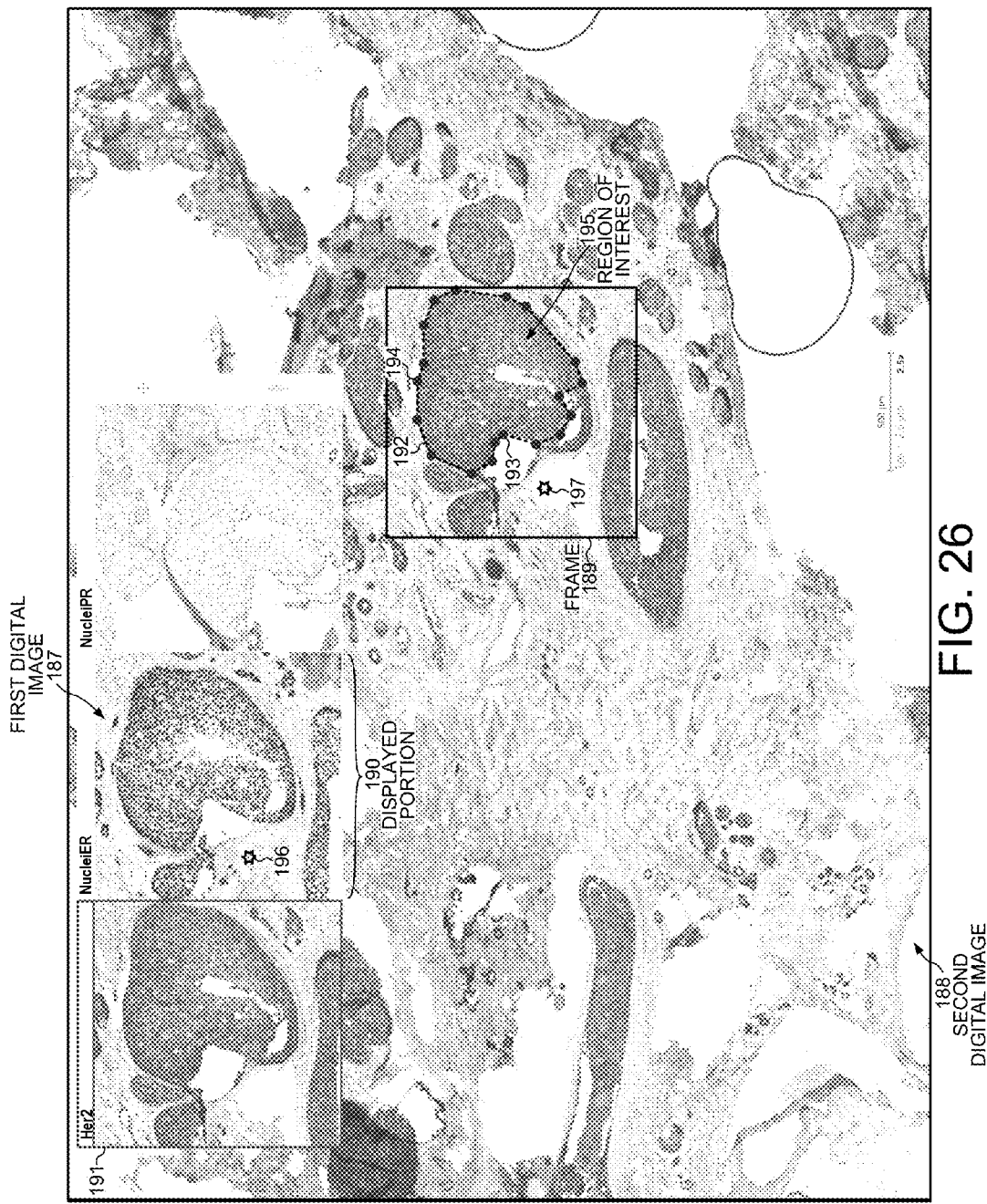
FIG. 26 shows a step of the method in which a user has manually drawn an outline around a region of interest on the digital image in the frame of FIG. 25.

FIG. 26 shows a step of the method in which the user of system 10, such as a pathologist, manually draws an outline 192 around a region of interest on second digital image 188. In one embodiment, outline 192 is generated on second digital image 188 by clicking a mouse button while the cursor is located at contour points around the periphery of the region of interest. System 10 then connects the contour points with lines to form outline 192. Two exemplary contour points 193-194 on outline 192 are labeled in FIG. 26. Outline 192 marks the region of interest 195, which is a tissue structure that has been stained with Human Epidermal growth factor Receptor 2 (Her2). In another embodiment, the user of system 10 positions outline 192 on second digital image 188 by clicking a mouse button while the cursor is located at contour points around the periphery of the region of interest. System 10 then generates a smooth outline that connects all of the contour points. In yet another embodiment, the user of system 10 manually draws outline 192 by dragging the cursor around the periphery of the region of interest while the mouse button is depressed. System 10 then adds contour points at inflection points along the outline. In an additional embodiment, the region of interest is the boundary between anatomical structures, such as the boundary of a growing cancerous region. Thus, the outline need not surround an enclosed area, but rather can be a curve such as the middle path 64 of FIG. 7D or middle path 151 of FIG. 19A.

FIG. 26 also shows a first landmark 196 on first digital image 187 and a corresponding second landmark 197 on second digital image 188. Many pairs of landmarks, including landmark pair 196-197, are used to coregister the pixels of first digital image 187 with the pixels of second image 188.

Figure 27:
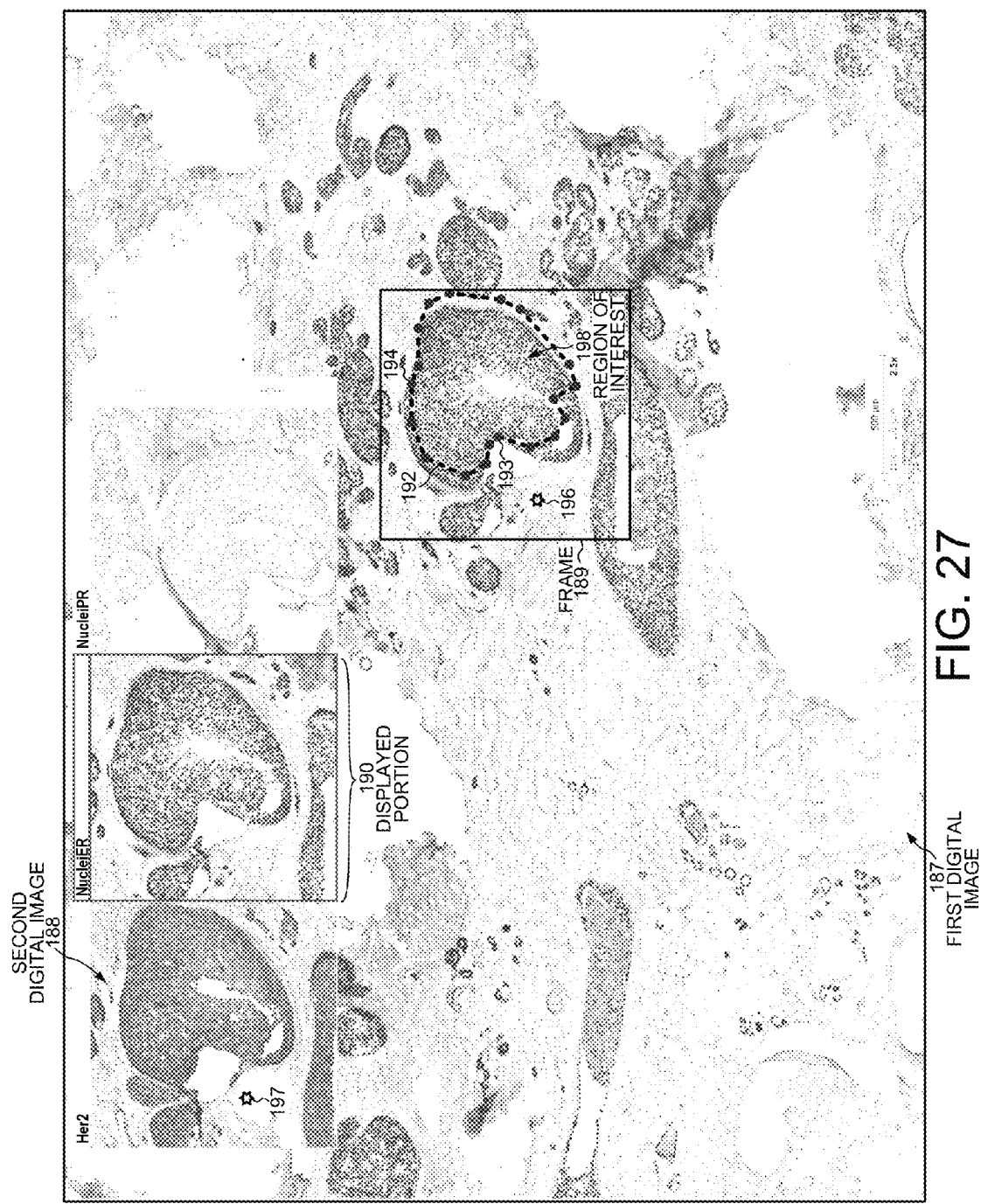
FIG. 27 illustrates a next step in which the user manually generates outlines around regions of interest on another digital image that is coarsely coregistered with the image in the frame of FIG. 25.

FIG. 27 illustrates a next step in which the user of system 10 now manually generates outlines around regions of interest on first digital image 187. In one embodiment, the user does not draw the outlines around the regions of interest from scratch but rather is presented with proposed outlines by system 10 based on the outlines previously drawn on second digital image 188. FIG. 27 shows outline 192, which was manually generated on second digital image 188 in FIG. 26, being positioned by system 10 onto first digital image 187. Outline 192 is positioned onto first digital image 187 using first landmark 196 and other first landmarks based on the coarse coregistration between the two images 187-188. Consequently, a first spatial relationship between outline 192 and first landmark 196 on first digital image 187 corresponds to a second spatial relationship between outline 192 and second landmark 197 on second digital image 188.

It is evident from FIG. 27 that outline 192 deviates somewhat from the periphery of the corresponding tissue structure that is the probable region of interest 198 in first digital image 187. This indicates that the landmarks, including first landmark 196, near region of interest 198 in first digital image 187 are inaccurately positioned probably due to local distortions in the tissue slice. System 10 provides the user with a means for repositioning and modifying the outline 192 to better designate the region of interest 198 on first digital image 187. System 10 then uses the corrected outline 192 to update the landmarks near the region of interest 198 and thereby to improve the coregistration of first and second digital images 187-188.

Figure 28:
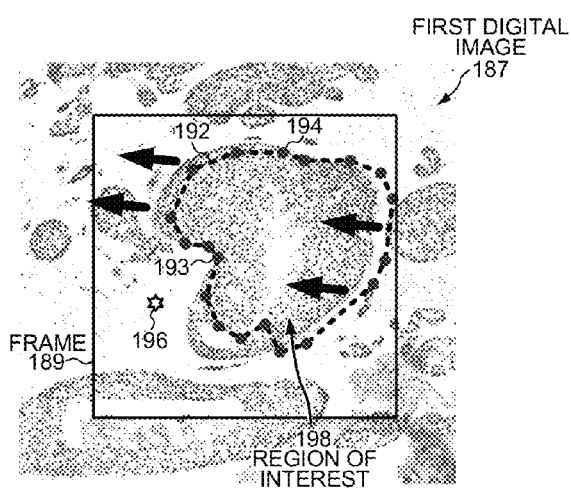
FIG. 28 shows a portion of the image of FIG. 27 in a next step in which the user manually corrects an outline around a region of interest by shifting the outline.

FIG. 28 shows a portion of first digital image 187 around frame 189 in a next step in which the user of system 10 manually corrects the outlines around regions of interest in first digital image 187. The user manually shifts outline 192 to overlap better with region of interest 198. In this example, the user clicks on outline 192 and drags the outline to the left. In another embodiment, system 10 shifts outline 192 to a proposed best fit over region of interest 198.

Figure 29:
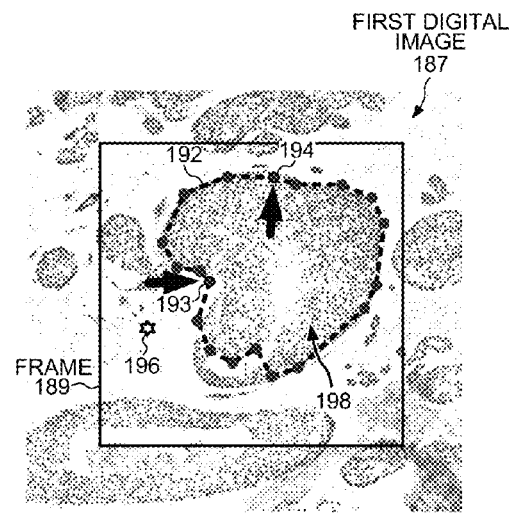
FIG. 29 shows how the user has manually corrected contour points on the outline of FIG. 28 to overlap better with the region of interest.

FIG. 29 shows outline 192 positioned over region of interest 198. It is apparent that the tissue structure of the region of interest has changed shape somewhat between the tissue slices depicted in the first and second digital images 187-188. For example, contour points 193-194 are no longer on the boundary of the region of interest 198. Contour point 193 is outside of the region of interest, while contour point 194 is inside the region of interest. The user now manually moves contour point 193 and contour point 194 on outline 192 to form a corrected outline 199 of the region of interest on first digital image 187. In this example, the user drags contour point 193 to the right and moves contour point 194 upwards.

Figure 30:
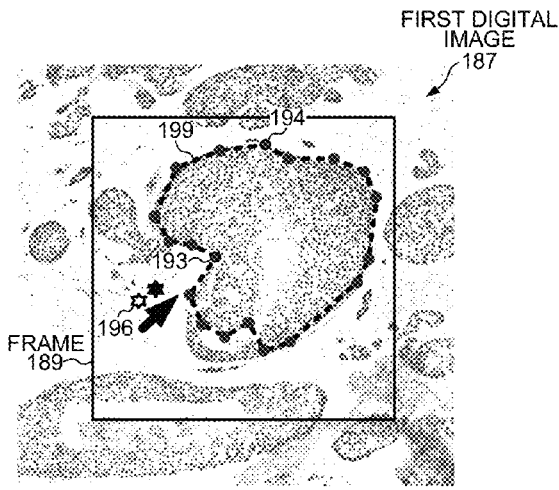
FIG. 30 shows the corrected outline displayed over the region of interest in the image of FIG. 27.

FIG. 30 shows corrected outline 199 displayed on first digital image 187 on graphical user interface 14. System 10 updates the first landmarks, including first landmark 196, based on how the user manually moves the contour points 193-194. The user does not move or correct the landmarks. Thus, system 10 moves first landmark 196 upwards and to the right on first digital image 187. Based on how the corrected contour points are manually moved, first landmark 196 on first digital image 187 is moved such that a first spatial relationship between corrected outline 199 and first landmark 196 corresponds to a second spatial relationship between outline 192 and second landmark 197.

Figure 31:
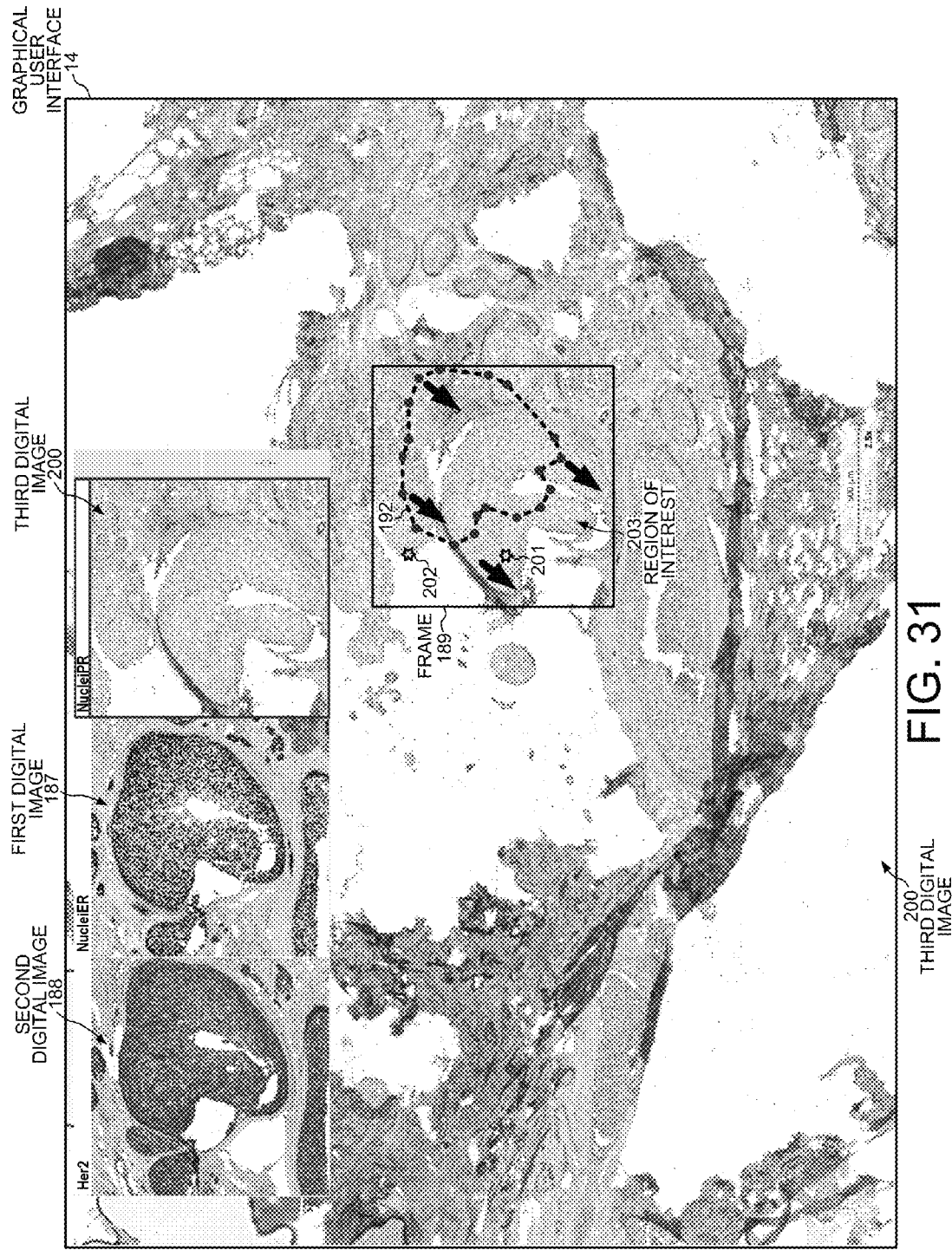
FIG. 31 illustrates the step in which landmarks on a third digital image are automatically updated as the user marks the regions of interest on the third image that is coarsely coregistered with the image in the frame of FIG. 25.

As the pathologist marks regions of interest on the images of the various tissue slices, the landmarks on those images are updated and the coregistration of the pixels in the vicinity of the updated landmarks is improved. No separate step of manually correcting landmarks is required. FIG. 31 illustrates the first step in which the landmarks on a third digital image 200 are automatically updated as the user of system 10 marks the regions of interest on the third image. Outline 192 that the user drew on second digital image 188 is added to third digital image 200 as the user shifts the associated portion of the third image inside the frame 189. System 10 locates the proposed outline using landmarks 201-202 based on the existing coarse coregistration between second digital image 188 and third digital image 200. The pathologist then shifts outline 192 downward and to the left so as to overlap the region of interest 203. The original landmarks 201-202 are also shifted along with outline 192. Then the landmarks 201-202 are adjusted again by system 10 as the pathologist corrects the contour points on outline 192 to fall on the periphery of the region of interest 203. The landmarks 201-202 are thereby updated, and the coregistration between pixels of the second and third digital images 188, 200 is improved as the pathologist marks the regions of interest in the third digital image 200.

Figures 32, 33:
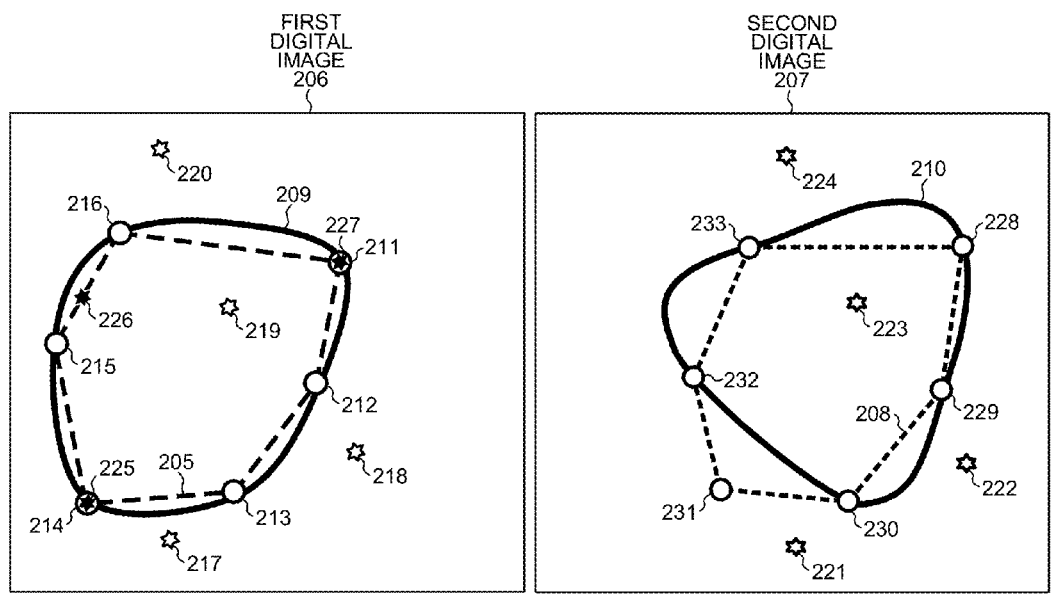
FIG. 32 shows an outline that the user has drawn around a region of interest on a first digital image of a first tissue slice.
FIG. 33 shows an outline that the system proposes on a second digital image of a second tissue slice based on the outline that the user marked on the first digital image in FIG. 32.
Figures 34, 35:
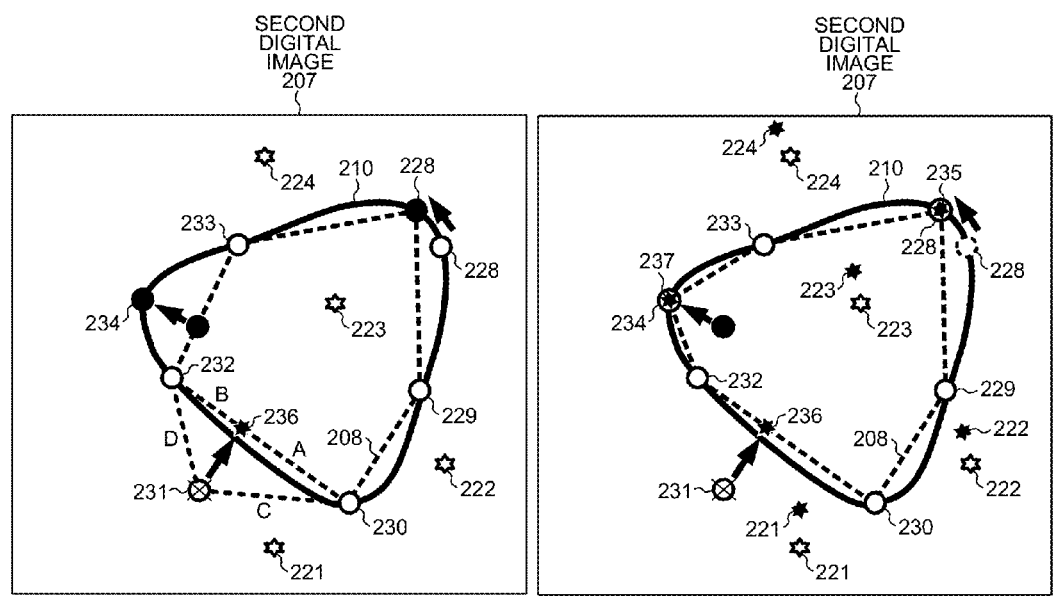
FIG. 34 illustrates how the user generates a corrected outline by shifting a contour point, deleting a contour point and adding a contour point on the outline.
FIG. 35 illustrates how the system uses the manual correction of the outline around the region of interest to update and add pairs of landmarks on the first and second digital images.

FIGS. 32-35 illustrate in more detail the steps by which a user of system 10 moves, adds and deletes contour points on outlines that the system proposes on a new digital image on which the pathologist has not already marked the regions of interest. FIG. 32 shows the dashed outline 205 that the user has drawn around a region of interest on a first digital image 206 of a first tissue slice. FIGS. 33-35 show how the user can correct the dashed outline 208 that the system proposes for the second digital image 207 of a second tissue slice based on the outline 205 that the user marked on the first digital image 206. The solid line 209 represents the anatomical boundary of the region of interest, such as the boundary of a cancer tumor, in the first digital image 206. The solid line 210 represents the boundary of the same anatomical structure in a different tissue slice, which is somewhat distorted compared to the anatomical boundary in first digital image 206.

Outline 205 is a polygon whose vertices are the contour points 211-216 around the periphery of the anatomical region of interest that the user has marked using a computer mouse and cursor. The open stars represent first landmarks 217-220 that system 10 generates using image analysis. Each of the first landmarks 217-220 on first digital image 206 is paired with one of the corresponding second landmarks 221-224 on the second digital image 207 of FIGS. 33-35. The black stars represent first landmarks 225-227 that are added by system 10 based on user input as the pathologist marks the regions of interest on coregistered digital images. But all of the landmarks are hidden from the user and are updated or added by system 10 in the background.

FIG. 33 shows the proposed outline 208 that system 10 has superimposed over the region of interest 210 on second digital image 207. The vertices 228-233 correspond to the vertices 211-216 of outline 205, but have been shifted somewhat based on the locations of second landmarks 221-224. The user of system 10 recognizes that the proposed outline 208 does not entirely correspond to the periphery of the region of interest. In order better to mark the region of interest, the user adds, deletes and moves contour points on the outline 208 to generate a corrected outline. For example, the user adds a contour point between existing contour points 232-233; the user deletes contour point 231; and the user shifts contour point 228 more towards a natural inflection point on the periphery of the region of interest.

FIG. 34 illustrates how the user generates the corrected outline 208 by shifting contour point 228, deleting contour point 231 and adding a contour point 234 between existing contour points 232-233. The user clicks on contour point 228 and drags it along the boundary 210 of the region of interest to a natural inflection point so that the linear sides of the polygonal outline 208 better follow the curved boundary of the region of interest. The user deletes contour point 231, which is well outside the boundary of the region of interest, by double clicking on the point. A linear side of the polygonal outline 208 is then formed between contour points 230 and 232. The user adds new contour point 234 between existing contour points 232-233 by clicking on the line between points 232-233 and dragging the cursor to a natural inflection point on the boundary 210 of the region of interest. Corrected outline 208 now has an additional vertex.

FIG. 35 illustrates how system 10 uses the manual correction of the outline around the region of interest to update and add pairs of landmarks on the first and second digital images 206-207. Because the user has shifted contour point 228 to a location that is confirmed to be both on the boundary 210 of the region of interest and at an inflection point on that boundary, system 10 creates a pair of new landmarks 227 and 235 at the locations of the contour points 211 and 228 on the first and second digital images 206-207, respectively. When the user deletes contour point 231 so that the line between remaining contour points 230 and 232 better follows the boundary 210 of the region of interest, system 10 creates a pair of new landmarks 225 and 236 on the first and second digital images 206-207, respectively. New first landmark 225 is located at the contour point 214 on outline 205 that corresponds to the contour point 231 that was deleted from outline 208. New second landmark 236 is located along the line between contour points 230 and 232 at a location that is the same relative distance between points 230 and 232 as the deleted point 231 was from points 230 and 232. Thus, in FIG. 34, the ratio of the distances A:B equals the ratio of the distances C:D.

Similarly, when the user adds contour point 234 between contour points 232-233, system 10 creates a pair of new landmarks 226 and 237 on the first and second digital images 206-207, respectively. New second landmark 237 is located at the new contour point 234 that was added to outline 208. As shown in FIG. 32, new first landmark 226 is located along the line between contour points 215-216 at a location that is the same relative distance between points 215-216 as the added point 234 is from points 232-233. In addition, the locations of the existing second landmarks 221-224 are updated based on how the user manually moved, added and deleted contour points on the proposed outline 208. The black stars 221-224 show the updated locations of the second landmarks 221-224, whose original locations are designated by white stars.

Figures 36, 37:
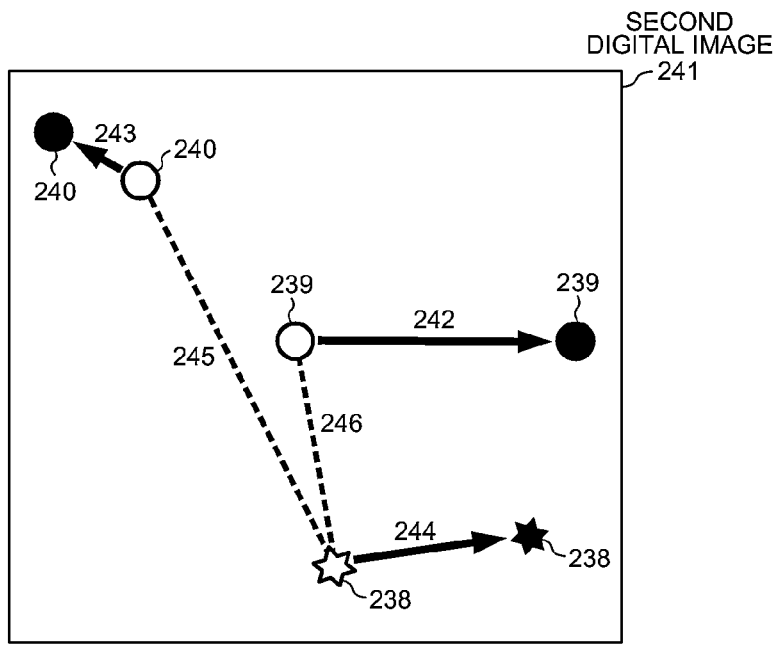
FIG. 36 shows how an existing landmark on the second image is updated based on how the user manually corrects contour points on an outline of a region of interest on the second image.
FIG. 37 shows equations used to calculate a more complex weighting of the landmark offset vector by which landmarks are corrected based on the distance to contour points that are corrected.

FIG. 36 illustrates how an existing second landmark 238 is updated based on how the user manually corrects contour points 239-240 on an outline of a region of interest on a second digital image 241 of a second tissue slice. The white star designates the location of second landmark 238 after image analysis coarsely coregisters the second digital image 241 with a first digital image. The black star shows the location of second landmark 238 after the user corrects the outline of the region of interest, and system 10 more finely coregisters the two digital images based on the user's manual correction of the contour points. The user corrects contour point 239 by shifting the point to the location of the black circle in the direction and distance indicated by the displacement vector 242. Similarly, the user corrects contour point 240 by moving the point to the upper left to the location of the black circle in the direction and distance indicated by the displacement vector 243. System 10 then updates the location of second landmark 238 in the direction and distance of landmark offset vector 244, which is a weighted sum of the vectors 242-243. The vectors 242-243 are weighted inversely proportional to their distances from second landmark 238. Because the distance 245 between landmark 238 and point 240 is about twice the distance 246 between landmark 238 and point 239, the displacement vector 242 at which point 239 was shifted has twice the weighting as the displacement vector 243 at which the point 240 was shifted. Landmark offset vector 244 is calculated based on the weighted contribution of the displacement vectors for all contour points that the user has corrected. By updating and adding new second landmarks on the second digital image, pixels in the vicinity of the updated and new landmarks are more finely coregistered by giving closer landmarks a greater weighting.

FIG. 37 shows equations 247-251 used to calculate a more complex weighting of the landmark offset vector ΔM by which landmarks are corrected based on the magnitude of each displacement vector τ (tau) and the distance d from the landmark $M_i$ to each contour point $P_j$ that is corrected. Equation 247 shows that the landmark offset vector ΔM for each landmark $M_i$ equals the weighted sum of the product for each contour point $P_j$ of the distance weighting factor w times the closeness weighting factor r times the displacement vector τ. Thus, the distance from the landmark to the contour point is factored in twice to the landmark offset vector, both in the distance weighting factor w and in the closeness weighting factor r. The distance weighting factor, however, is also dependent on the magnitude of the displacement vector. Equation 248 shows that the distance weighting factor is small if either or both the displacement vector is small or the distance to the contour point is large. Equation 249 shows that the closeness weighting factor is small if the relative distance between the corrected contour point and the landmark is large compared to the distances between the other contour points and the landmark. Equation 250 expresses the displacement vector between a corrected contour point Q and an original contour point P on the first image that is superimposed on the second image by the system transformation function T. T(P) designates the position of a superimposed control point before being shifted by the user. Equation 251 expresses the distance between the original location of a second landmark M and an original contour point P on the first image that is superimposed on the second image by the system transformation function T.

System 10 allows prior manual corrections to the contour points of proposed outlines to be saved and retrieved. A subsequent user of system 10 can return to an earlier version or state of updated landmarks based on prior corrections made to the contour points. For example, a subsequent pathologist may wish to correct the proposed outlines in a different manner. Thus, system 10 provides an "undo" functionality by saving the history of all landmark updates in database 12. A landmark on each digital image has a different instance for each coregistration state. After the user exits the screen of the graphical user interface 14 on which contour points have been moved, added or deleted, system 10 saves the locations of the contour points and the resulting updated landmarks as a new coregistration state. After coarse coregistration is completed using image analysis, the coregistration state is zero. For example, the corrections made to contour points 193-194 shown in FIG. 29. and the resulting updated position of landmark 196 are saved as an additional coregistration state after the user exits the graphical user interface screen as shown in FIG. 30. A subsequent user can return to the coregistration state shown in FIG. 30 or to the prior coregistration state shown in FIG. 28.

Although the present invention has been described in connection with certain specific embodiments for instructional purposes, the present invention is not limited thereto. Accordingly, various modifications, adaptations, and combinations of various features of the described embodiments can be practiced without departing from the scope of the invention as set forth in the claims.

What is claimed is:

1. A method comprising:
 segmenting a first digital image of a first tissue slice to generate first objects corresponding to tissue stained with a first stain;
 segmenting a second digital image of a second tissue slice to generate second objects corresponding to tissue stained with a second stain;
 coregistering the first digital image and the second digital image to generate a first landmark on the first digital image and a corresponding second landmark on the second digital image, wherein the second digital image is coarsely coregistered to the first digital image;
 manually outlining a first region of interest on the first digital image;
 projecting an outline of a second region of interest onto the second digital image using the second landmark;
 manually moving a contour point on the outline of the second region of interest to form a corrected outline of the second region of interest;
 displaying the corrected outline of the second region of interest on the graphical user interface; and
 moving the second landmark based on how the contour point was manually moved.

2. The method of claim 1, wherein the second digital image is more finely coregistered to the first digital image after the second landmark is moved.

3. The method of claim 1, further comprising:
 displaying the second digital image on the graphical user interface such that an area of the second digital image is enclosed by a first frame;
 displaying a portion of the first digital image on the graphical user interface in a second frame, wherein the first frame and the second frame are equally sized and shaped, and wherein the displayed portion of the first digital image corresponds to the area of the second digital image that is enclosed by the first frame; and
 shifting the portion of the first digital image that is displayed in the second frame such that the first landmark is located within the second frame at a location corresponding to where the second landmark is located in the first frame after being moved.

4. The method of claim 1, wherein the first region of interest corresponds to a tumor region of the tissue stained with the first stain.

5. The method of claim 1, wherein the second landmark has an original location that falls within a first coregistration state upon the second digital image being coarsely coregistered, and wherein the second landmark has a new location after the moving the second landmark, further comprising:
 saving the new location of the second landmark and a first moved location of the contour point on the corrected outline as part of a second coregistration state;
 manually moving the contour point of the outline an additional time; and returning to the second coregistration state by displaying the contour point at the first moved location of the second coregistration state.

6. The method of claim 1, wherein the contour point has a revised location after the manually moving the contour point, and wherein the second landmark has a new location after the moving the second landmark, further comprising:
saving the new location of the second landmark;
manually moving the contour point on the outline an additional time; and
displaying the contour point at the revised location using the saved new location of the second landmark.

7. The method of claim 1, wherein the second region of interest is a boundary between anatomical structures, wherein the outline is a curve, and wherein the contour point falls on the curve.

8. A method comprising:
displaying a first digital image of a first tissue slice on a graphical user interface such that an area of the first digital image is enclosed by a frame, wherein the displayed portion of the first digital image is larger than the frame;
displaying a portion of a second digital image of a second tissue slice on the graphical user interface, wherein the first tissue slice and the second tissue slice are both z slices taken from a tissue sample at corresponding positions in the x and y dimensions, wherein the displayed portion of the second digital image has a shape of the frame, wherein the area of the first digital image that is enclosed by the frame corresponds to the displayed portion of the second digital image, wherein the area of the first digital image that is enclosed by the frame is coarsely coregistered with the displayed portion of the second digital image;
positioning an outline of a region of interest on the first digital image, wherein the outline was manually generated on the second digital image, wherein a first spatial relationship between the outline on the first digital image and a first landmark on the first digital image corresponds to a second spatial relationship between the outline on the second digital image and a second landmark on the second digital image;
manually moving a contour point on the outline on the first digital image to form a corrected outline of the region of interest on the first digital image;
displaying the corrected outline on the first digital image on the graphical user interface; and
based on how the contour point was manually moved, moving the first landmark on the first digital image such that the first spatial relationship between the corrected outline on the first digital image and the first landmark corresponds to the second spatial relationship between the outline on the second digital image and the second landmark on the second digital image.

9. The method of claim 8, wherein the area of the first digital image that is enclosed by the frame is more finely coregistered with the displayed portion of the second digital image after the first landmark is moved.

10. The method of claim 8, further comprising:
shifting the displayed portion of the second digital image that has the shape of the frame such that the second landmark is located in the displayed portion at a location corresponding to where the first landmark is located in the frame after being moved.

11. The method of claim 8, wherein the second digital image having the shape of the frame is displayed in a coregistered orientation to how the area of the first digital image that is enclosed by the frame is displayed.

12. The method of claim 8, wherein the region of interest corresponds to a tumor region on the first tissue slice.

13. A method comprising:
displaying a first digital image of a first tissue slice on a graphical user interface;
displaying a second digital image of a second tissue slice on the graphical user interface, wherein the first tissue slice is stained with a first biomarker and the second tissue slice is stained with a second biomarker, wherein the first digital image is coarsely coregistered with the second digital image using a first landmark on the first digital image and a second landmark on the second digital image;
positioning an outline over a second region of interest on the second digital image using the second landmark, wherein the outline was manually drawn over a first region of interest on the first digital image;
manually moving a first contour point of the outline on the second digital image to form a corrected outline;
displaying the corrected outline over the second region of interest on the graphical user interface; and
moving the second landmark based on how the first contour point was manually moved, wherein the first digital image is more finely coregistered with the second digital image after the second landmark is moved.

14. The method of claim 13, wherein the first region of interest corresponds to a tumor region on the first tissue slice.

15. The method of claim 13, further comprising:
generating a statistical value for the second region of interest, wherein the statistical value is a staining score taken from the group consisting of: an Her2 score, an Allred score, a Gleason score, and an Elston-Ellis score.

16. The method of claim 13, wherein the first digital image is coregistered with the second digital image by coregistering a first pixel of the first digital image with a second pixel of the second digital image using the first landmark and the second landmark.

17. The method of claim 13, further comprising:
manually moving a second contour point of the outline on the second digital image to form the corrected outline; and
moving the second landmark based on how both the first contour point and the second contour point were manually moved, wherein how a contour point is manually moved has a greater influence on the moving of the second landmark the closer the contour point is to the second landmark.

18. The method of claim 13, wherein the second landmark has an original location that falls within a first coregistration state upon the second digital image being coarsely coregistered with the first digital image, and wherein the second landmark has a new location after the moving the second landmark, further comprising:
saving the new location of the second landmark and a first moved location of the moved contour point as part of a second coregistration state;
manually moving the contour point of the outline an additional time; and
returning to the second coregistration state by displaying the moved contour point at the first moved location.

19. The method of claim 13, wherein the first contour point has a first moved location after the manually moving, and wherein the second landmark has a new location after the moving the second landmark, further comprising:
saving the new location of the second landmark;

manually moving the first contour point of the outline an additional time; and displaying the first contour point at the first moved location using the saved new location of the second landmark.

20. The method of claim 13, wherein the first contour point has a first moved location after the manually moving, further comprising:

adding a third landmark to the second digital image at the first moved location.

* * * * *